US010525322B2

(12) United States Patent
Balakrishnan et al.

(10) Patent No.: US 10,525,322 B2
(45) Date of Patent: Jan. 7, 2020

(54) ACTION DETECTION AND ACTIVITY CLASSIFICATION

(71) Applicant: NIKE, Inc., Beaverton, OR (US)

(72) Inventors: SantoshKumar Balakrishnan, Hillsboro, OR (US); Jordan M. Rice, Portland, OR (US); Steven H. Walker, Camas, WA (US); Adam S. Carroll, Bend, OR (US); Corey C. Dow-Hygelund, Sunriver, OR (US); Aaron K. Goodwin, Bend, OR (US); James M. Mullin, Bend, OR (US); Tye L. Rattenbury, New York, NY (US); Joshua M. Rooke-Ley, New York, NY (US); John M. Schmitt, Bend, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 16/508,553

(22) Filed: Jul. 11, 2019

(65) Prior Publication Data

US 2019/0329118 A1  Oct. 31, 2019

Related U.S. Application Data

(63) Continuation of application No. 15/254,548, filed on Sep. 1, 2016, now Pat. No. 10,384,113, which is a (Continued)

(51) Int. Cl.
*A63B 71/06* (2006.01)
*G09B 19/00* (2006.01)
(Continued)

(52) U.S. Cl.
CPC .............. *A63B 71/06* (2013.01); *A41D 1/002* (2013.01); *A43B 3/0005* (2013.01); *A61B 5/0002* (2013.01); *A61B 5/0004* (2013.01); *A61B 5/0022* (2013.01); *A61B 5/0059* (2013.01); *A61B 5/0077* (2013.01); *A61B 5/01* (2013.01); *A61B 5/02438* (2013.01); *A61B 5/1112* (2013.01); *A61B 5/1118* (2013.01); *A61B 5/1123* (2013.01); *A61B 5/486* (2013.01); *A61B 5/681* (2013.01); *A61B 5/6807* (2013.01); *A61B 5/7246* (2013.01); *A61B 5/7257* (2013.01); *A61B 5/7264* (2013.01); *A61B 5/7282* (2013.01); *A61B 5/742* (2013.01); *A61B 5/7475* (2013.01); *A63B 24/0003* (2013.01); *A63B 24/0062* (2013.01); *A63B 24/0075* (2013.01);
(Continued)

(58) Field of Classification Search
CPC combination set(s) only.
See application file for complete search history.

(56) References Cited

U.S. PATENT DOCUMENTS

| 8,344,876 | B2* | 1/2013 | Brown | H04Q 9/00 340/539.13 |
|---|---|---|---|---|
| 2014/0066816 | A1* | 3/2014 | McNames | A61B 5/002 600/595 |
| 2014/0306821 | A1* | 10/2014 | Rahman | G05B 1/01 340/539.11 |

* cited by examiner

*Primary Examiner* — Reginald A Renwick
(74) *Attorney, Agent, or Firm* — Banner & Witcoff, Ltd.

(57) ABSTRACT

Activities, actions and events during user performance of physical activity may be detected using various algorithms and templates. Templates may include an arrangement of one or more states that may identify particular event types and timing between events. Templates may be specific to a particular type of activity (e.g., types of sports, drills, events, etc.), user, terrain, time of day and the like.

20 Claims, 26 Drawing Sheets

Related U.S. Application Data continuation of application No. 15/060,899, filed on Mar. 4, 2016, now Pat. No. 9,456,781, which is a continuation of application No. 14/571,664, filed on Dec. 16, 2014, now Pat. No. 9,314,685, which is a continuation of application No. 13/401,592, filed on Feb. 21, 2012, now Pat. No. 9,352,207.

(60) Provisional application No. 61/588,608, filed on Jan. 19, 2012.

(51) Int. Cl.

| | |
|---|---|
| *A61B 5/00* | (2006.01) |
| *A41D 1/00* | (2018.01) |
| *G16H 40/67* | (2018.01) |
| *G16H 20/30* | (2018.01) |
| *G09B 5/12* | (2006.01) |
| *A63B 24/00* | (2006.01) |
| *A43B 3/00* | (2006.01) |
| *A61B 5/01* | (2006.01) |
| *A61B 5/024* | (2006.01) |
| *G09B 5/00* | (2006.01) |
| *A61B 5/11* | (2006.01) |
| *G09B 5/02* | (2006.01) |
| *G16H 20/40* | (2018.01) |

(52) U.S. Cl.
CPC ............... *G09B 5/00* (2013.01); *G09B 5/02* (2013.01); *G09B 5/125* (2013.01); *G09B 19/003* (2013.01); *G09B 19/0038* (2013.01); *G16H 20/30* (2018.01); *G16H 20/40* (2018.01); *G16H 40/67* (2018.01); *A61B 2503/10* (2013.01); *A61B 2562/029* (2013.01); *A61B 2562/0219* (2013.01); *A61B 2562/0252* (2013.01); *A61B 2562/08* (2013.01); *A63B 2024/0065* (2013.01)

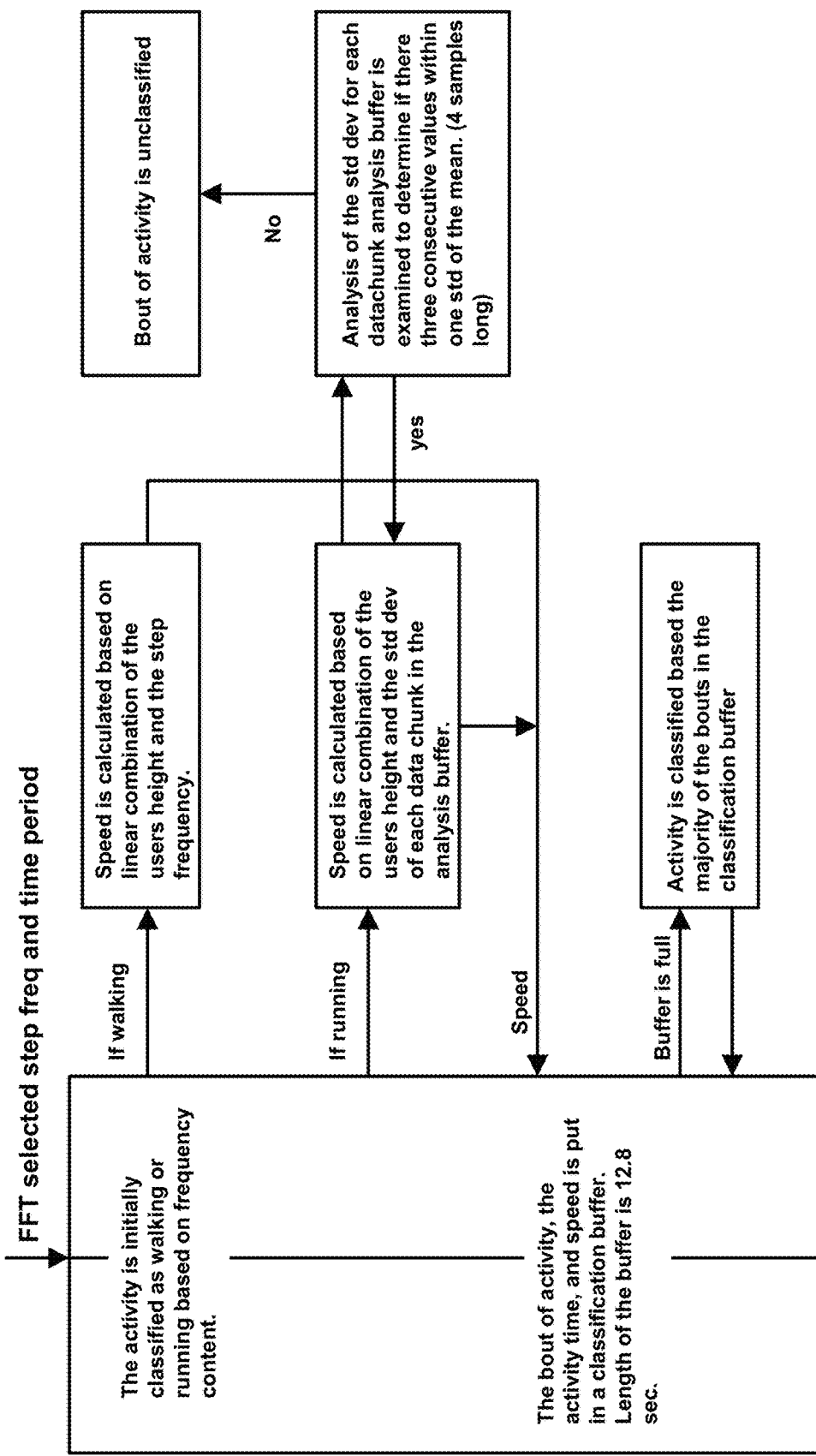

```
{
    "name":"Jump - Two Foot Launch, Right Strike",          1400
    "template-states":
    [
        [
            0,"LEFT_STRIKE",
            -1,-600,"ESP_DIST_INCREASING",0,0,0,0,
            0,0,0,0,0,0,
            0,0,0,0,0,0,
            0,0,0,0,0,0
        ],
        [
            1,"RIGHT_STRIKE",
            0,-250,"ESP_DIST_ABSVAL_DECREASING",200,300,400,500,
            0,0,0,0,0,0,
            0,0,0,0,0,0,
            0,0,0,0,0,0
        ],
        [
            2,"LEFT_LAUNCH",
            1,-250,"ESP_DIST_ABSVAL_DECREASING",200,300,400,500,
            0,0,0,0,0,0,
            0,0,0,0,0,0,
            0,0,0,0,0,0
        ],
        [
            3,"RIGHT_LAUNCH",
            1,-250,"ESP_DIST_ABSVAL_DECREASING",200,300,400,500,
            0,0,0,0,0,0,
            0,0,0,0,0,0,
            0,0,0,0,0,0
        ],
        [4,"RIGHT_STRIKE",1,3],
        [5,"RIGHT_LAUNCH",1,3],
        [6,"LEFT_STRIKE",0,2],
        [7,"LEFT_LAUNCH",0,2]
    ]
}
```

1401a: first block (LEFT_STRIKE)
1401b: second block (RIGHT_STRIKE)
1401c: third block (LEFT_LAUNCH)
1401d: fourth block (RIGHT_LAUNCH)
1401e: [4,"RIGHT_STRIKE",1,3]
1401f: [5,"RIGHT_LAUNCH",1,3]
1401g: [6,"LEFT_STRIKE",0,2]
1401h: [7,"LEFT_LAUNCH",0,2]

FIG. 14

ACTION DETECTION AND ACTIVITY CLASSIFICATION

CROSS-REFERENCE TO RELATED APPLICATION

This application is a continuation of U.S. application Ser. No. 15/254,548, filed Sep. 1, 2016, which is a continuation of U.S. application Ser. No. 15/060,899, filed Mar. 4, 2016, now U.S. Pat. No. 9,456,781, which is a continuation of U.S. application Ser. No. 14/571,664 filed Dec. 16, 2014, now U.S. Pat. No. 9,314,685, which is a continuation of U.S. application Ser. No. 13/401,592, filed Feb. 21, 2012, now U.S. Pat. No. 9,352,207, which claims the benefit of priority from U.S. Provisional Application No. 61/588,608, filed Jan. 19, 2012. The content of the above noted applications are hereby incorporated herein by reference in their entirety.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interest are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of this disclosure relate to activity classification values. In certain embodiments, activity classification may be calculated. One or more devices may use an accelerometer and/or other sensors to monitor activity of a user. Under certain implementations, activity classification of a user may be estimated for different activities.

According to one aspect, user actions during performance of an activity may be detected based on templates that specify matching versus non-matching patterns of events. In one example, templates may be defined by a plurality of constraints which must be matched. Additionally or alternatively, template constraints may define exclusions configured to remove one or more events from consideration as a potential match.

In some embodiments, the present invention can be partially or wholly implemented on a computer-readable medium, for example, by storing computer-executable instructions or modules, or by utilizing computer-readable data structures.

Of course, the methods and systems of the above-referenced embodiments may also include other additional elements, steps, computer-executable instructions, or computer-readable data structures.

The details of these and other embodiments are set forth in the accompanying drawings and the description below. Other features and advantages will be apparent from the description and drawings, and from the claims.

BRIEF DESCRIPTION OF THE DRAWINGS

The present disclosure is illustrated by way of example and not limited in the accompanying figures in which like reference numerals indicate similar elements and in which:

FIGS. 1A-B illustrate an example of a system for providing personal training in accordance with example embodiments, wherein FIG. 1A illustrates an example network configured to monitor athletic activity, and FIG. 1B illustrates an example computing device in accordance with example embodiments;

FIG. 8 shows an example flowchart that may be implemented to classify activity and determine speed in accordance with one embodiment;

FIG. 14 illustrates an example action template;

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

I. Example Personal Training System

A. Illustrative Computing Devices

Figure 1A:
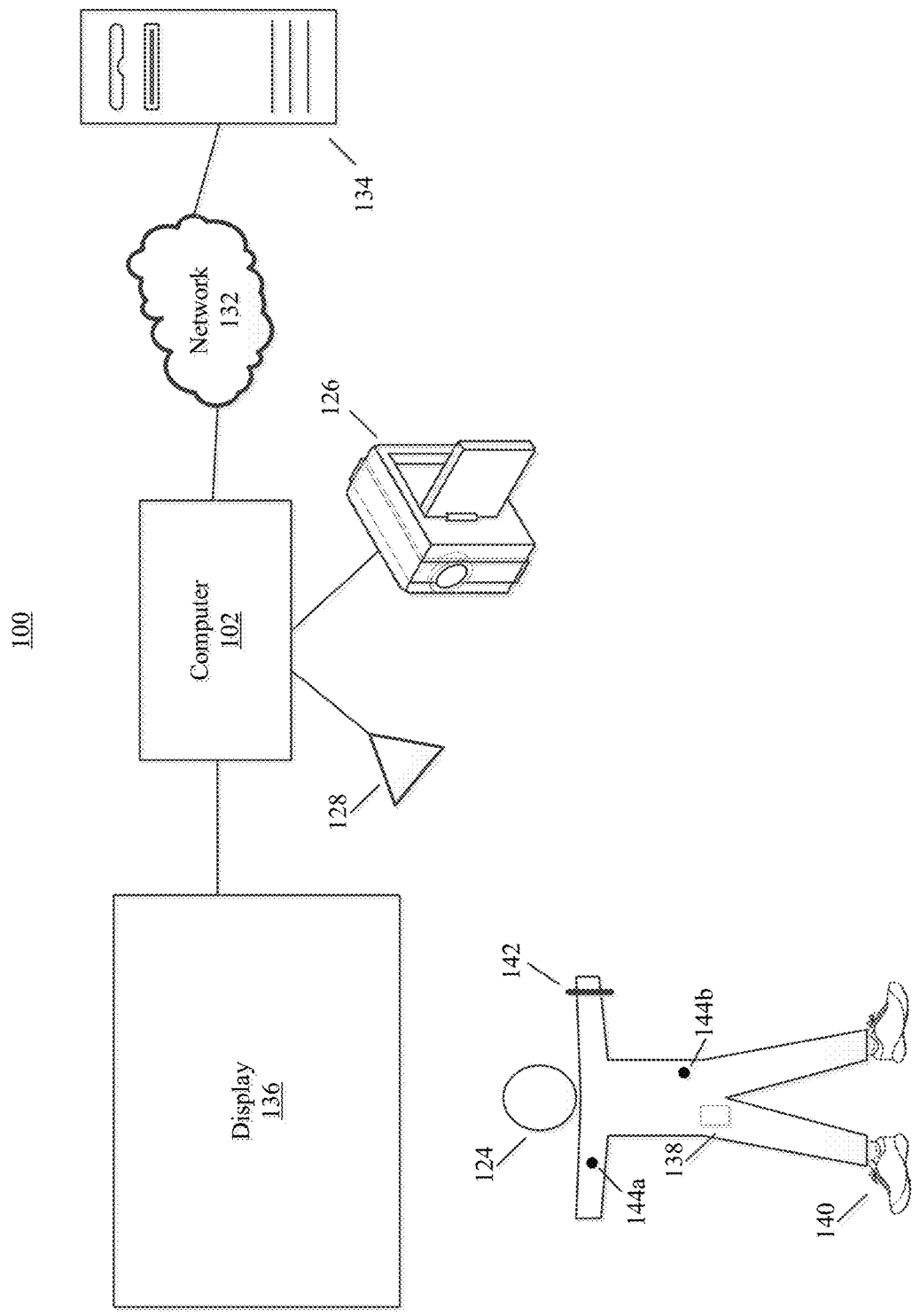

FIG. 1A illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® Playstation, and/or a Nintendo® Wii gaming consoles. Those skilled in the art will appreciate that these are merely example consoles for descriptive purposes and this disclosure is not limited to any console or device.

Figure 1B:
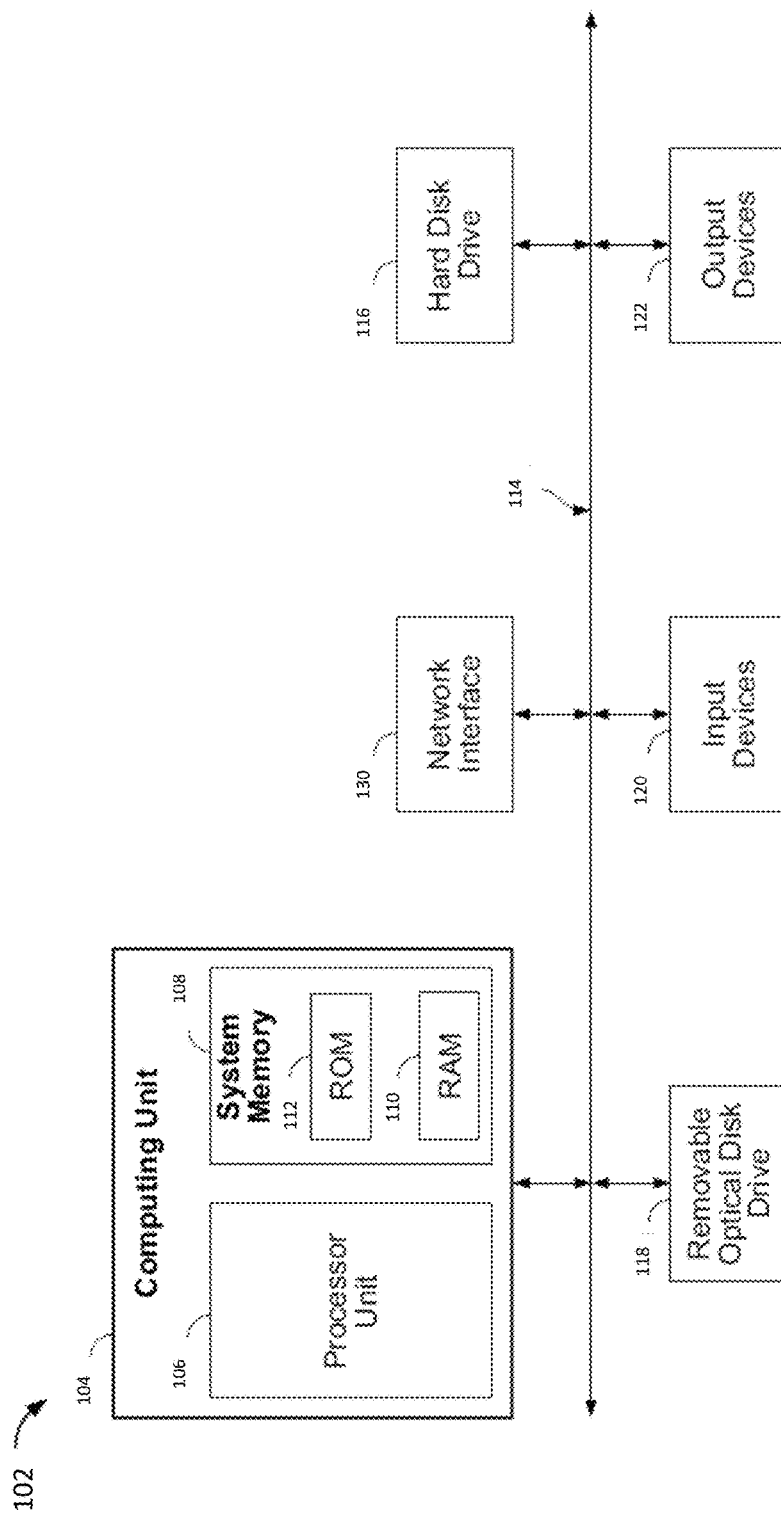

Turning briefly to FIG. 1B, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card. The processing unit 106 and the system memory 108 also may be directly or indirectly connected to one or more input devices 120 and one or more output devices 122. The output devices 122 may include, for example, a display device 136, television, printer, stereo, or speakers. In some embodiments one or more display devices may be incorporated into eyewear. The display devices incorporated into eyewear may provide feedback to users. Eyewear incorporating one or more display devices also provides for a portable display system. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1A.

Looking again to FIG. 1A, image-capturing device 126 and/or sensor 128 may be utilized in detecting and/or measuring athletic movements of user 124. In one embodiment, data obtained from image-capturing device 126 or sensor 128 may directly detect athletic movements, such that the data obtained from image-capturing device 126 or sensor 128 is directly correlated to a motion parameter. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

B. Illustrative Network

Computer 102, computing unit 104, and/or any other electronic devices may be directly or indirectly connected to one or more network interfaces, such as example interface 130 (shown in FIG. 1B) for communicating with a network, such as network 132. In the example of FIG. 1B, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topology(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1A. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

C. Illustrative Sensors

Computer 102 and/or other devices may comprise one or more sensors 126, 128 configured to detect and/or monitor at least one fitness parameter of a user 124. Sensors 126 and/or 128 may include, but are not limited to: an accelerometer, a gyroscope, a location-determining device (e.g., GPS), light sensor, temperature sensor (including ambient temperature and/or body temperature), sleep pattern sensors, heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oreg. Although image capturing device 126 and sensor 128 and display 136 are shown in direct (wirelessly or wired) communication with computer 102, those skilled in the art will appreciate that any may directly communicate (wirelessly or wired) with network 132.

1. Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144a-b. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub, No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Devices 138-144 may communicate with each other, either directly or through a network, such as network 132. Communication between one or more of devices 138-144 may take place via computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 1B may be included in the server 134, other computers, apparatuses, etc.

2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

i. Shoe-Mounted Device

In certain embodiments, sensory device 140 may comprise footwear which may include one or more sensors, including but not limited to: an accelerometer, location-sensing components, such as GPS, and/or a force sensor system. FIG. 2A illustrates one example embodiment of a sensor system 202. In certain embodiments, system 202 may include a sensor assembly 204. Assembly 204 may comprise one or more sensors, such as for example, an accelerometer, location-determining components, and/or force sensors. In the illustrated embodiment, assembly 204 incorporates a plurality of sensors, which may include force-sensitive resistor (FSR) sensors 206. In yet other embodiments, other sensor(s) may be utilized. Port 208 may be positioned within a sole structure 209 of a shoe. Port 208 may optionally be provided to be in communication with an electronic module 210 (which may be in a housing 211) and a plurality of leads 212 connecting the FSR sensors 206 to the port 208. Module 210 may be contained within a well or cavity in a sole structure of a shoe. The port 208 and the module 210 include complementary interfaces 214, 216 for connection and communication. In one or more arrangements, electronic module 210 may be configured to perform sensor data processing (e.g., include one or more processors) and/or to provide sensory data (e.g., by including one or more additional sensors therein). In some arrangements, one or more of the sensors such as FSR sensor 206 may include individual processors for independently (e.g., separately from other sensors or types of sensors such as an accelerometer) processing sensor data and sending the processed data to electronic module 210 for aggregation and/or other processes.

In certain embodiments, at least one force-sensitive resistor 206 shown in FIG. 2A may contain first and second electrodes or electrical contacts 218, 220 and a force-sensitive resistive material 222 disposed between the electrodes 218, 220 to electrically connect the electrodes 218, 220 together. When pressure is applied to the force-sensitive material 222, the resistivity and/or conductivity of the force-sensitive material 222 changes, which changes the electrical potential between the electrodes 218, 220. The change in resistance can be detected by the sensor system 202 to detect the force applied on the sensor 216. The force-sensitive resistive material 222 may change its resistance under pressure in a variety of ways. For example, the force-sensitive material 222 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 222 may change the resistance by changing the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 222 and the electrode 218, 220 222 and/or the surface resistance between a conducting layer (e.g., carbon/graphite) and a force-sensitive layer (e.g., a semiconductor) of a multi-layer material 222. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 222, as defined herein, may be or include a doped or non-doped semiconducting material.

The electrodes 218, 220 of the FSR sensor 216 can be formed of any conductive material, including metals, carbon/graphite fibers or composites, other conductive composites, conductive polymers or polymers containing a conductive material, conductive ceramics, doped semiconductors, or any other conductive material. The leads 212 can be connected to the electrodes 218, 220 by any suitable method, including welding, soldering, brazing, adhesively joining, fasteners, or any other integral or non-integral joining method. Alternately, the electrode 218, 220 and associated lead 212 may be formed of a single piece of the same material.

Figure 2B:
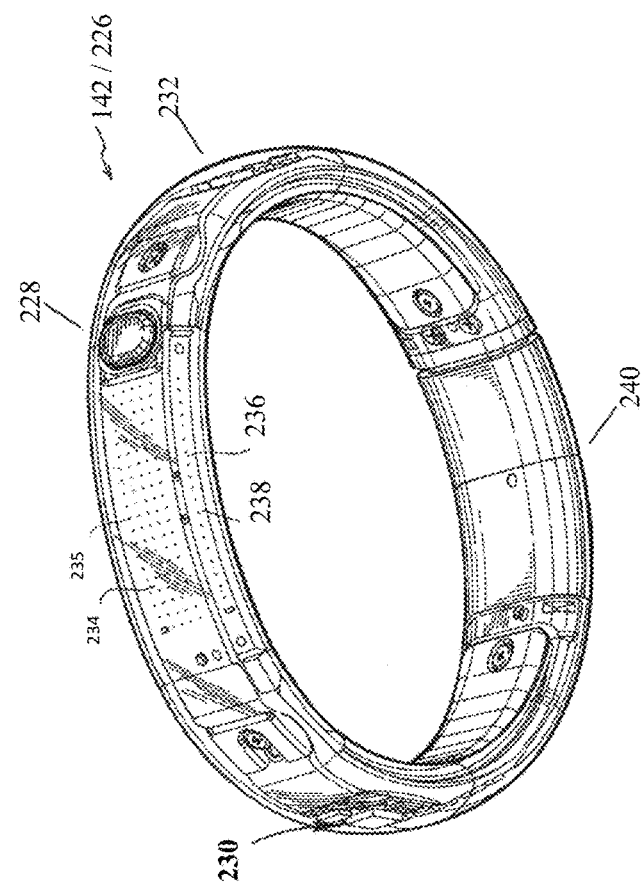
FIGS. 2A-C illustrate example sensor assemblies that may be worn by a user in accordance with example embodiments.
Figure 2A:
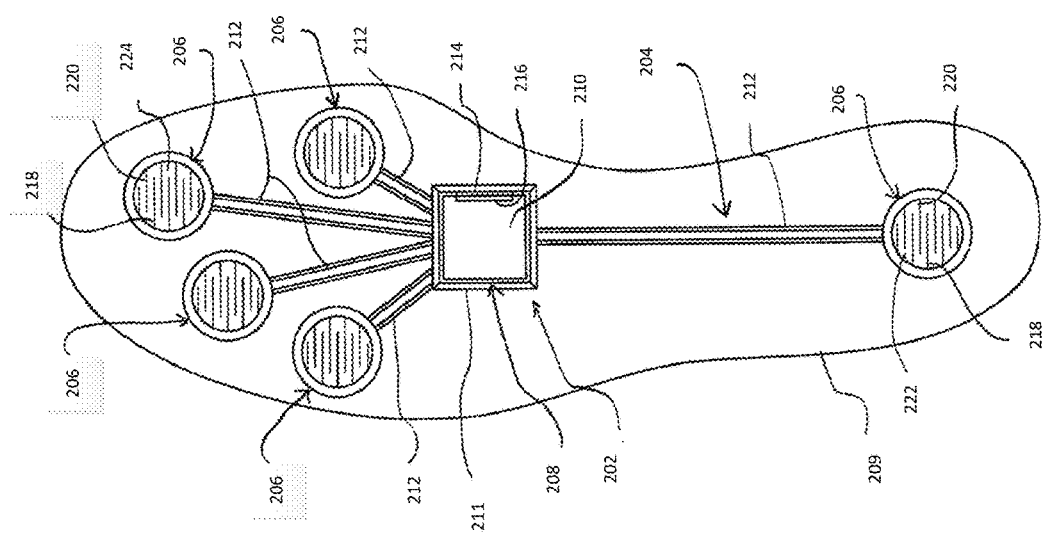
Figure 2C:
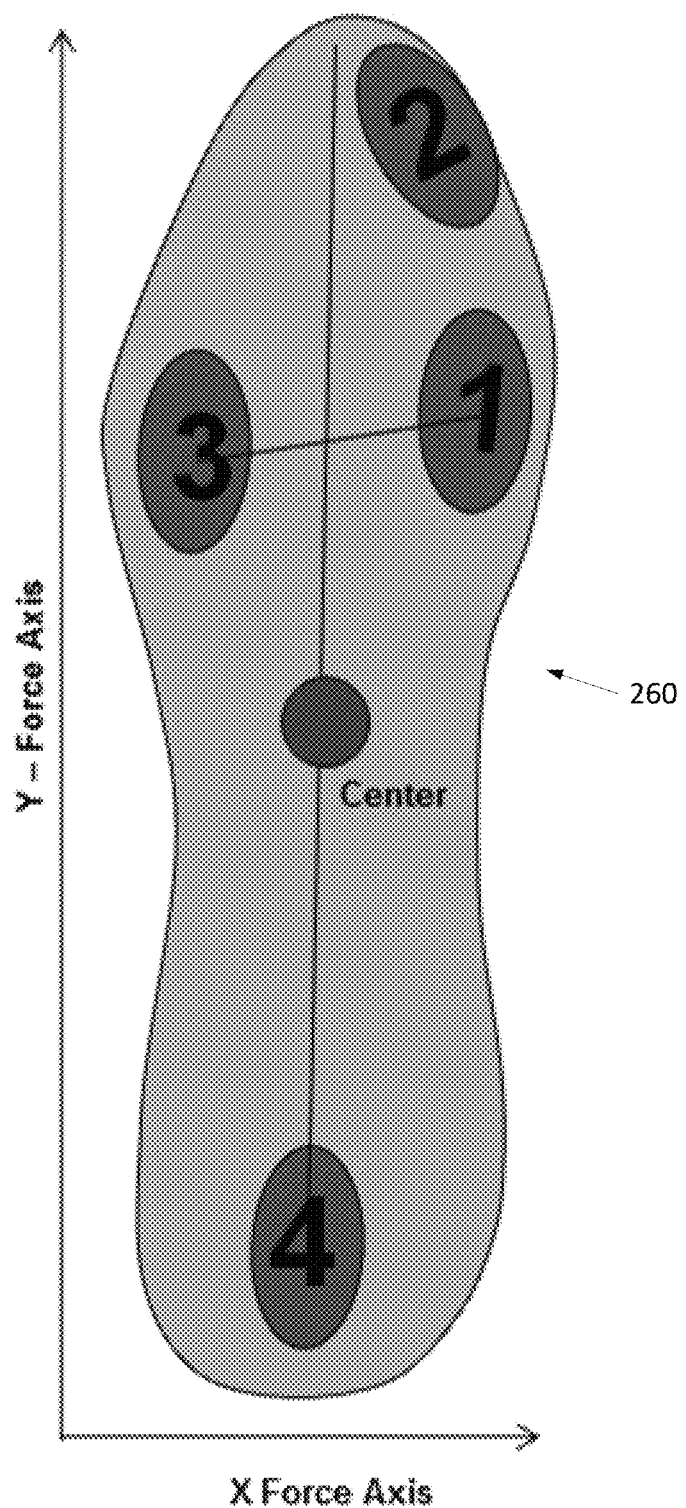

FIG. 2C illustrates another example arrangement of a shoe-based sensor system 260. The shoe-based sensor system 260 may comprise a plurality of force sensors such as force sensitive sensors 261 similar to those described above with respect to FIG. 2A. Sensor system 260 may differ from the arrangement of FIG. 2A in the number and placement of the force sensitive sensors 261. Using such force sensitive sensors 216 and 261, a device may be configured to determine a user's center of mass and detect shifts in weight. Such information may be useful in detecting various activity event characteristics including an amount of force with which a user's jumps, whether the user has centered his or her weight/mass for a particular drill, and/or a center of force when a user lands after jumping. As noted above, the force sensitive sensors 261 may be combined with one or more other types of shoe based sensors including accelerometers, gyroscopic sensors, thermometers, geographic location determination sensors, proximity sensors (e.g., to determine a proximity of the user's foot with the user's other foot or other portion of the user's body) and the like and/or combinations thereof. In one example, shoe based sensors may also be used in conjunction with one or more other sensor systems including wrist-worn sensor devices as described in further detail below.

ii. Wrist-Worn Device

As shown in FIG. 2B, device 226 (which may resemble or be sensory device 142 shown in FIG. 1A) may be configured to be worn by user 124, such as around a wrist, arm, ankle or the like. Device 226 may monitor athletic movements of a user, including all-day activity of user 124. In this regard, device assembly 226 may detect athletic movement during user's 124 interactions with computer 102 and/or operate independently of computer 102. For example, in one embodiment, device 226 may be an-all day activity monitor that measures activity regardless of the user's proximity or interactions with computer 102. Device 226 may communicate directly with network 132 and/or other devices, such as devices 138 and/or 140. In other embodiments, athletic data obtained from device 226 may be utilized in determinations conducted by computer 102, such as determinations relating to which exercise programs are presented to user 124. In one embodiment, device 226 may also wirelessly interact with a mobile device, such as device 138 associated with user 124 or a remote website such as a site dedicated to fitness or health related subject matter. At some predetermined time, the user may wish to transfer data from the device 226 to another location.

As shown in FIG. 2B, device 226 may include an input mechanism, such as a depressible input button 228 assist in operation of the device 226. The input button 228 may be operably connected to a controller 230 and/or any other electronic components, such as one or more of the elements discussed in relation to computer 102 shown in FIG. 1B. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234. It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140.

In certain embodiments, device 226 may comprise a sensor assembly (not shown in FIG. 2B). The sensor assembly may comprise a plurality of different sensors. In an example embodiment, the sensor assembly may comprise or permit operative connection to an accelerometer (including in the form of a multi-axis accelerometer), heart rate sensor, location-determining sensor, such as a GPS sensor, and/or other sensors. Detected movements or parameters from device's 142 sensor(s), may include (or be used to form) a variety of different parameters, metrics or physiological characteristics including but not limited to speed, distance, steps taken, and calories, heart rate, sweat detection, effort, oxygen consumed, and/or oxygen kinetics. Such parameters may also be expressed in terms of activity points or currency earned by the user based on the activity of the user.

II. Activity Classification

Certain aspects of this disclosure relate to classifying user activity, such as with one or more of the sensors of system 100. The activity may include athletic and/or other physical activity of user 124. Detected motion parameters may be utilized in one or more determinations relating to classifying activity. In accordance with a first embodiment, a plurality of samples from one or more sensors (e.g., sensors 126, 128, and/or 138-142) may be obtained during a first time period. In one embodiment, at least one sensor (e.g. sensor 142) comprises an accelerometer. The accelerometer may be a multi-axis accelerometer. In another embodiment, a plurality of accelerometers may be utilized. Other non-accelerometer based sensors are also within the scope of this disclosure, either in combination with an accelerometer or individually. Indeed, any sensor(s) configurable to detect or measure athletic movement and/or physiologic properties are within the scope of this disclosure. In this regard, data may be obtained and/or derived from a plurality of sensors, including for example, location sensors (e.g., GPS), heart rate sensors, force sensors, etc. In one embodiment, various systems and methods are implemented, at least partially, on a portable device. In certain embodiments, the portable device may be a wrist-worn device (see, e.g., sensor 142).

In one embodiment, detected parameters may be classified into one or more categories. Example categories may include, but are not limited to: running, walking, exercising, participating in a specific sport or activity, or combinations thereof.

Further aspects relate to detecting and/or measuring a quantity of steps taken by a user, such as user 124. In one embodiment, a quantity of steps may be detected during a predefined period of time. In another embodiment, detecting or measuring a quantity of steps may be utilized in a classification of motions by user 124 into one or more categories.

Detected motion parameters, such as but not limited to, a quantity of steps taken by a user, may be utilized to classify activity. In one embodiment, the frequency/quantity of steps may be utilized in the classification of activity, such as either walking or running, for example. In certain embodiments, if data cannot be categorized as being within a first category (e.g., walking) or group of categories (e.g., walking and running), a first method may analyze collected data. For example, in one embodiment, if detected parameters cannot be classified, then a Euclidean norm equation may be utilized for further analysis. In one embodiment, an average magnitude vector norm (square root of the sum of the squares) of obtained values may be utilized. In yet another embodiment, a different method may analyze at least a portion of the data following classification within a first category or groups of categories. In one embodiment, a step algorithm, such as those disclosed herein, may be utilized.

Further aspects of this disclosure relate to novel systems and methods that may be utilized to quantify steps, such as during walking or running, of a user. In certain embodiments, at least a portion of any quantifications or calculations may be conducted on a portable device, including a wrist-worn device (e.g., sensor 142). The novel systems and methods may, in certain embodiments, provide one or more benefits not obtained in prior art systems and methods, including for example: improved accuracy, decreased latency in reporting the values, improved classification of activities based upon step count (for example, proper classification for individuals who do not "bounce" during walking and/or running to the same extent as an "average" individual), excluding repetitive behavior from improperly being classified as a specific activity, such as for example, running and/or walking, determinations of intensity and/or speed and utilization of those determinations in activity classification, improved power consumptions, and/or combinations of these or other improvements.

Data may be obtained from one or more sensors, including either carried or worn by the user or those fixed in specific locations. In accordance with a first embodiment, a plurality of samples from one or more sensors may be obtained during a first time period. In one embodiment, at least one sensor comprises an accelerometer. The accelerometer may be a multi-axis accelerometer. In another embodiment, a plurality of accelerometers may be utilized. Other non-accelerometer based sensors are also within the scope of this disclosure. In one implementation, a fixed sampling rate may be utilized, yet in other embodiments, a variable sampling rate may be implemented for at least one of the sensors. In one embodiment, a 25 Hertz sampling rate may be utilized. In one such embodiment, utilizing a 25 Hz sampling rate to obtain accelerometer data from a wrist-worn portable device may adequately obtain data, such as for example, step counts while obtaining acceptable battery life as compared to other prior art methodologies. In yet another embodiment, a 50 Hz sampling rate may be utilized. Other rates are within the scope of this disclosure. In certain embodiments, the first time period may be 1 second. In one embodiment, 64 samples of data may be obtained during the first time period. In one embodiment, each sample of data may have multiple parameters, such as motion vectors for multiple axes, however, in other embodiments; each sample of data is a single value. Certain implementations may provide data comprising multiple values as a single value. For example, data from a 3-axis accelerometer may be provided as a single value.

The collected data may be analyzed or processed, which may occur upon collection, at predefined intervals, upon occurrence of predefined criteria, at a later time, or combinations thereof. In certain implementations, samples within the first time period may be mean centered and/scaled.

Samples (or data relating to the received samples) from the first time period may be placed in a buffer. Those skilled in the art realize that one or more buffers may be part of any one or more computer-readable mediums, such as computer-readable mediums 110 and/or 112 within system memory 108. One or more systems or methods may be implemented to determine whether samples from the first time period are placed in a first buffer. One or more factors may determine whether samples from the first time period are placed within a buffer. In one embodiment, accuracy and/or reliability may be considered.

In one embodiment, about 128 samples may be placed in a first buffer. In another embodiment, the buffer duration may differ. In certain embodiments, the buffer may be about twice (e.g., 2×) the first time period. For example, if the first time period is 1 second, then the buffer duration may be 2 seconds in certain embodiments. The buffer may be a specific time duration (e.g., 2 seconds) regardless of the duration of the first time period. The buffer duration may depend on one or more factors, including for example but not limited to: battery life, desired energy consumption, sampling rate, samples obtained, a desired wait time before calculation procedures and/or combinations thereof among other considerations.

In certain implementations, the first buffer may comprise one or more sub-buffers. For example, a 128 sample buffer at a sample rate of 25 Hz may comprise two 64 sample sub-buffers. In one embodiment, each sub-buffer is independently analyzed from at least one other sub-buffer (and may be independently buffered from each other sub-buffer in that particular buffer).

Further aspects of this disclosure relate to classifying data that may be discarded before conducting further analysis (such as for example, Fourier Transform (FFT) analysis). In one embodiment, the first buffer may have data indicative of motion or other physical activity, for example, accelerometer data (alone or in combination with data from one or more other sensors) may comprise frequencies indicative of detected activity. The activity, however, may not be activity comprising steps. In yet other embodiments, steps may be detected, however, the detected steps may not signify an activity as to which the device is configured to detect. For example, a device (or plurality of devices) may be configured to detect walking and/or running, but not a shuffling motion commonly performed in a sporting environment. In this regard, activity within several sports may cause the user to swing their arms and/or bounce, however, are not indicative of walking or running. For example, a defensive basketball player often has to shuffle in several directions, however, is not walking or running. Aspects of this disclosure relate to increasing the accuracy of step counting, and therefore, may implement processes to remove such movements from step counting determinations. These activities, however, may be considered in further analysis, such as for a determination of activity classification. In accordance with one embodiment, the first buffer (or any other collection of data) may undergo a classification process. In one embodiment, the collection of data (i.e., the first buffer which may be 128 samples over a duration of 5 seconds) may be divided into smaller sections (sub-buffers). In one embodiment, the first buffer may be subdivided into 4 equal sub-buffers (which may be, for example, a half second in duration). In one embodiment, each sub-buffer may be about half a second, regardless of the size of the buffer.

Further analysis (and/or other statistical measures) may be made on the sub-buffers, such as for example, calculating an average (e.g., a mean value) and/or a deviation (e.g., variation or standard deviation) of data within a sub-buffer. Data within a sub-buffer may be compared with a threshold. As used herein, discussions relating to a threshold may refer to being lower and/or higher than a predetermined value or range of values. In one embodiment, an average value may be compared with a first threshold. In one implementation, if the data within the sub-buffer does not meet a threshold, then data within an entire buffer (e.g., the first buffer) may not be utilized in further determinations of step quantification. Further logic may be utilized to determine if the sub-buffers have valid data (e.g., data that met the threshold), and if so, that data is utilized in further step count determinations. In certain embodiments, the data of the first buffer (as opposed to the individual sub-buffers) is utilized in further determinations.

If the buffer (e.g., the first buffer) meets the threshold (and/or passes other criteria, including but not limited to those described in the preceding paragraph), that data may be utilized. In one embodiment, this data may be placed in an analysis buffer. In one embodiment, non-mean centered data obtained during the corresponding duration of the acceptable first buffer may be provided to the analysis buffer, which may be a first-in last-out (FILO). The analysis buffer may comprise the same duration as the first buffer. In one embodiment, the analysis buffer comprises 5 seconds in duration of data. The buffer may comprise 128 samples.

Further aspects of this disclosure relate to systems and methods for locating peaks within activity data. In one embodiment, peak locating systems and methods may be utilized on data within a buffer, such as the analysis buffer. Yet in other embodiments, peaks may be located within any other data. In one embodiment, one or more processes may be utilized to locate peaks. For example, a first method may be utilized to locate peaks within a fixed range. Yet in certain embodiments, a second method may be utilized to determine identification criteria for locating peaks. In certain implementations, the first, second or additional methods may be implemented based, at least in part, on battery life. For example, the second method may require additional processing power, and therefore, may not be utilized upon receiving an indication that the battery life was decreased below a set point, and/or is declining at a rate above a threshold.

One or more systems or methods for determining identification criteria for locating peaks may estimate frequency of the data points. For example, an average (such as for example, a mean value) and/or a standard deviation (or variance) may be obtained. Such data may be utilized to determine "peaks" and "valleys" (e.g., the high and low values within the data), which may be quantified. Such data may be used in determinations of dynamic thresholds and/or derivative around the peak.

Further systems and methods may identify peaks (and/or valleys) on thresholds. In this regard, computer-executable instructions of one or more non-transitory computer-readable mediums may be executed to determine if a threshold quantity of peaks are located within the range (either fixed or dynamically determined). If no peaks within the range are located, that buffer may be emptied (or otherwise not utilize that data in step counting determinations). In this regard, the peaks may refer to the frequencies may be measured by those with the highest quantity of occurrences and/or highest absolute value.

As would be appreciated in the art there may be situations in which the data (e.g., frequencies) change, however, the user may still be conducting the same activity, albeit at a different rate or pace. For example, if a user is running at 10 mph and slows to 5 mph, he/she may still running, although at a slower pace. In this situation, however, the frequency detected will be altered. Certain embodiments may utilize linear combinations to quantify steps. For example, if a previous data indicated that the user was walking or running the next set of data may utilize the prior data in any determinations, such as in a linear combination. In one embodiment, if there are a first quantity of sections of the buffer duration that are classified as "running" and a second quantity of section classified as "walking", systems and methods may be utilized to determine whether the user has merely adjusted their stride or otherwise changed their speed. In one embodiment, at least a portion of the samples within the buffer may be deemed to be within a specific category regardless of the data for that portion. For example, if samples were collected for 10 intervals and 9 of them were classified as running and only a single one was classified as walking, then the entire duration may be deemed running. In one embodiment, an interval may only be deemed a different category if it is immediately preceded and/or proceeded by data indicative of a consistently different category.

In certain embodiments, an indication that the user is not walking, running or performing another predetermined activity, may cease utilizing linear combinations of data in step counting determinations. For example, this may occur when a user has ceased stepping (e.g., no longer walking or running). Thus, systems and methods may cease any linear combination processes. In one embodiment, step quantification may be determined absent linear combinations, such as for example, by identifying peaks as discussed above.

Certain embodiments relate to selecting a sub-group (or sub-groups) of peaks within the frequency data to utilize in the determinations of step quantification. In one embodiment, a specific peak (or peaks) within the data (such as for example, data obtained within the first buffer and/or data obtained during first time frame) may be utilized. This may be conducted based upon determining that linear combination cannot be used. In one embodiment, "bounce peaks," "arm swing peaks," and/or other peaks may be identified. For example, many users "bounce" upon landing their feet when running. This bounce may provide frequency peaks within the data. Other peaks (and/or valleys) may be present within the sensor data. For example, many users often swing their arms in a predictable manner during running and/or walking to provide "arm swing peaks". For example, arms usually swing along an anterior/posterior axis (e.g., front to back). This frequency may be about half the frequency of the "bounce peaks". These peaks, however, may each vary independently, based upon, for example, the individual, the type of motion, the terrain, and/or a combination thereof. In accordance with one embodiment, systems and methods may be utilized to select which peaks are to be utilized in further analysis.

Data within the identified peaks and valleys or otherwise meeting a threshold may be utilized to determine if the quantified steps are running or walking. In certain embodiments, the "signature" of the signals may be utilized in determining whether the user was walking or running (or perhaps, conducting another activity). In one embodiment, signals within the range of 0.5-2.4 Hz may be considered as indicative of walking. In another embodiment, signals within the range of 2.4 to 5 Hz may be considered as indicative of running. In one embodiment, changing may be determined based upon the frequency and the sum of the standard deviation for 2 portions of data. In one embodiment, this (and/or other data) may be examined to determine whether a plurality of consecutive values are within a standard deviation of the mean. In one embodiment, this analysis may be conducted over a plurality of samples.

Further embodiments may utilize data regardless of whether that data is considered to be indicative of running or walking. In one embodiment, data may be utilized to systems and methods for determining activity classification. Systems and methods for determining activity classification may utilize this (and other) data to categorize the sensed data into an activity. In one embodiment, the first buffer discussed above, may be utilized, however, in other embodiments; a separate "activity" buffer may be utilized that has a different duration than first buffer. Although, an activity buffer may have a different duration than a first buffer, there is no requirement that these (or other) buffers are distinct buffers, rather the second buffer may be a collection of several first buffers and or a logical extension of other buffers. In this regard, collected data may be stored in a single location but utilized (even simultaneously for two different buffers, processes, and/or analyses).

In one embodiment, an activity buffer may be about 12.8 seconds in duration. Yet other durations are within the scope of this disclosure. If the entire (or substantially the entire duration) was consistent, such as for example, 1 second intervals within the duration indicated the user was walking or conducting a consistent activity, then a first default process may be utilized to determining activity. In one embodiment, a Euclidean mean value may be calculated based upon the consistent data.

Figure 3:
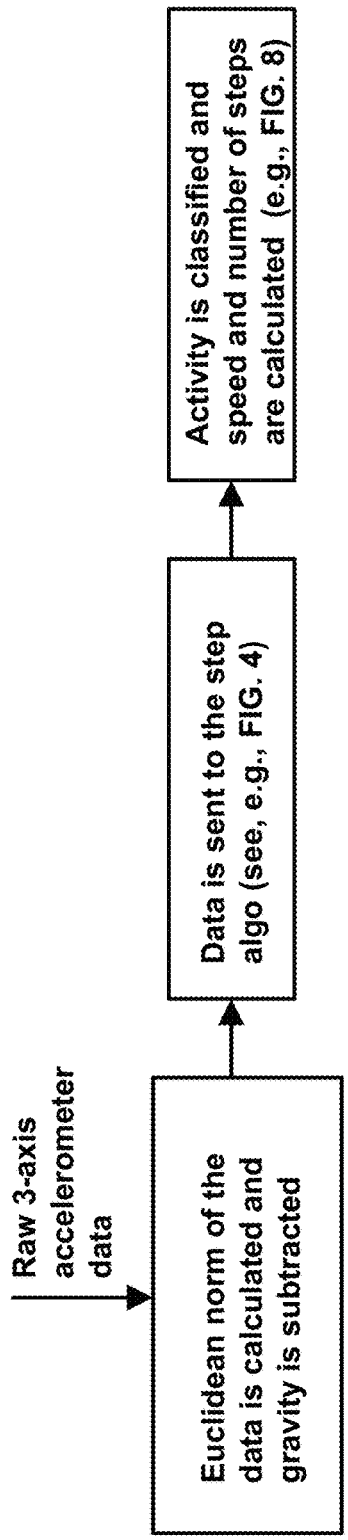
FIG. 3 illustrates an example method that may be utilized to classify activity classification, in accordance with an embodiment of the invention.
Figure 4:
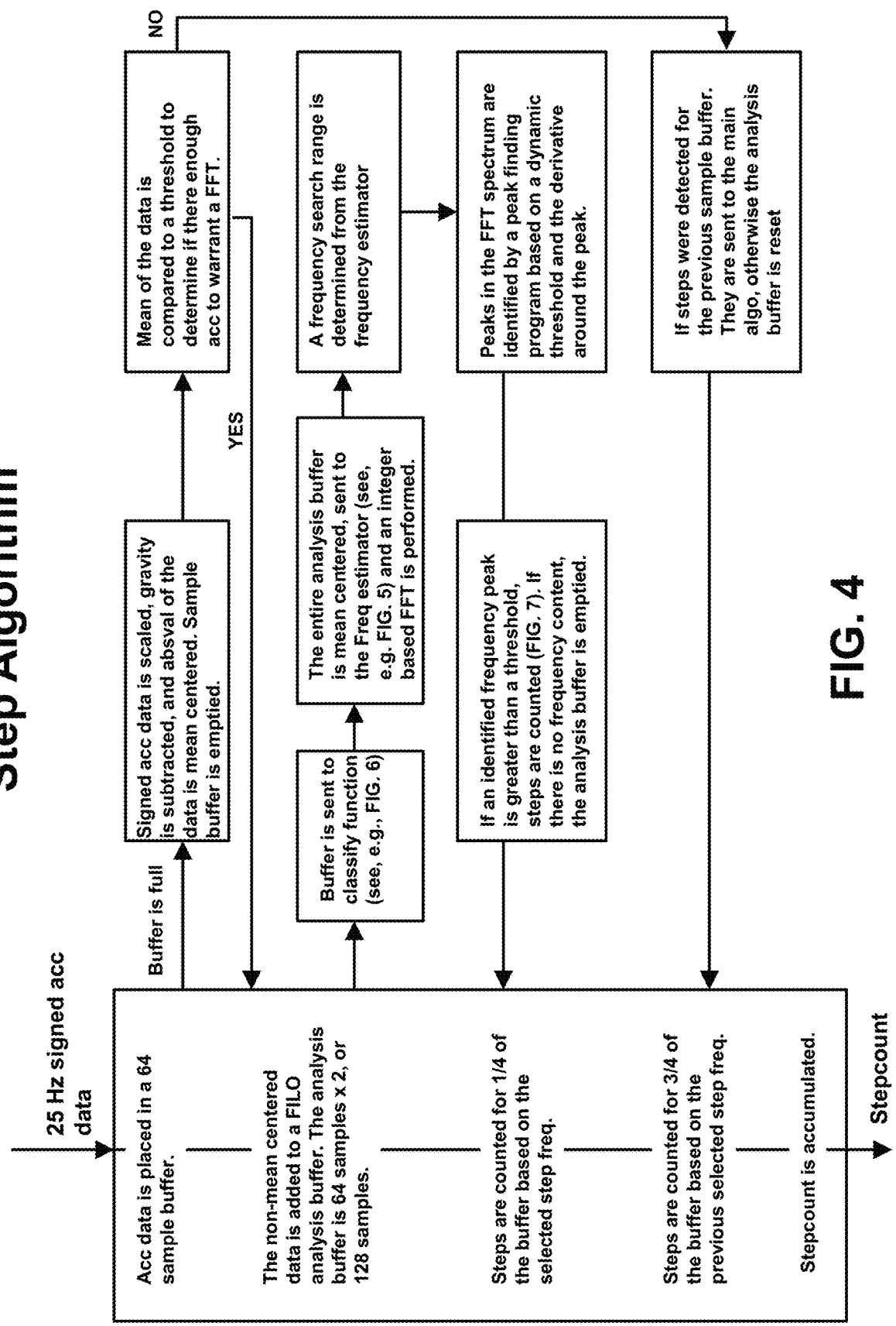
FIG. 4 shows an example flowchart that may be utilized to quantify steps in accordance with one embodiment.
Figure 5:
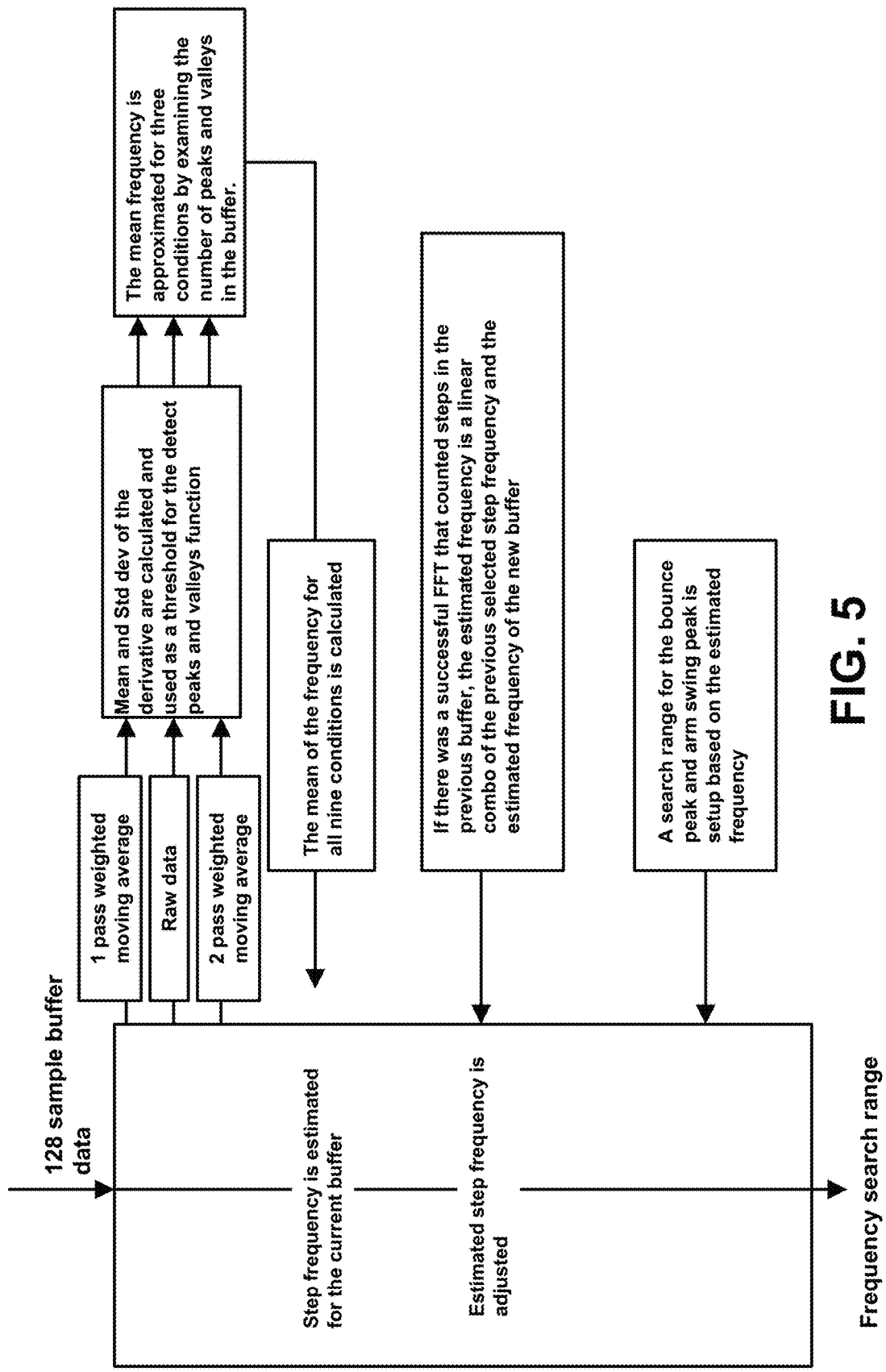
FIG. 5 shows an example flowchart that may estimate frequency and set up a frequency search range in accordance with one embodiment.
Figure 6:
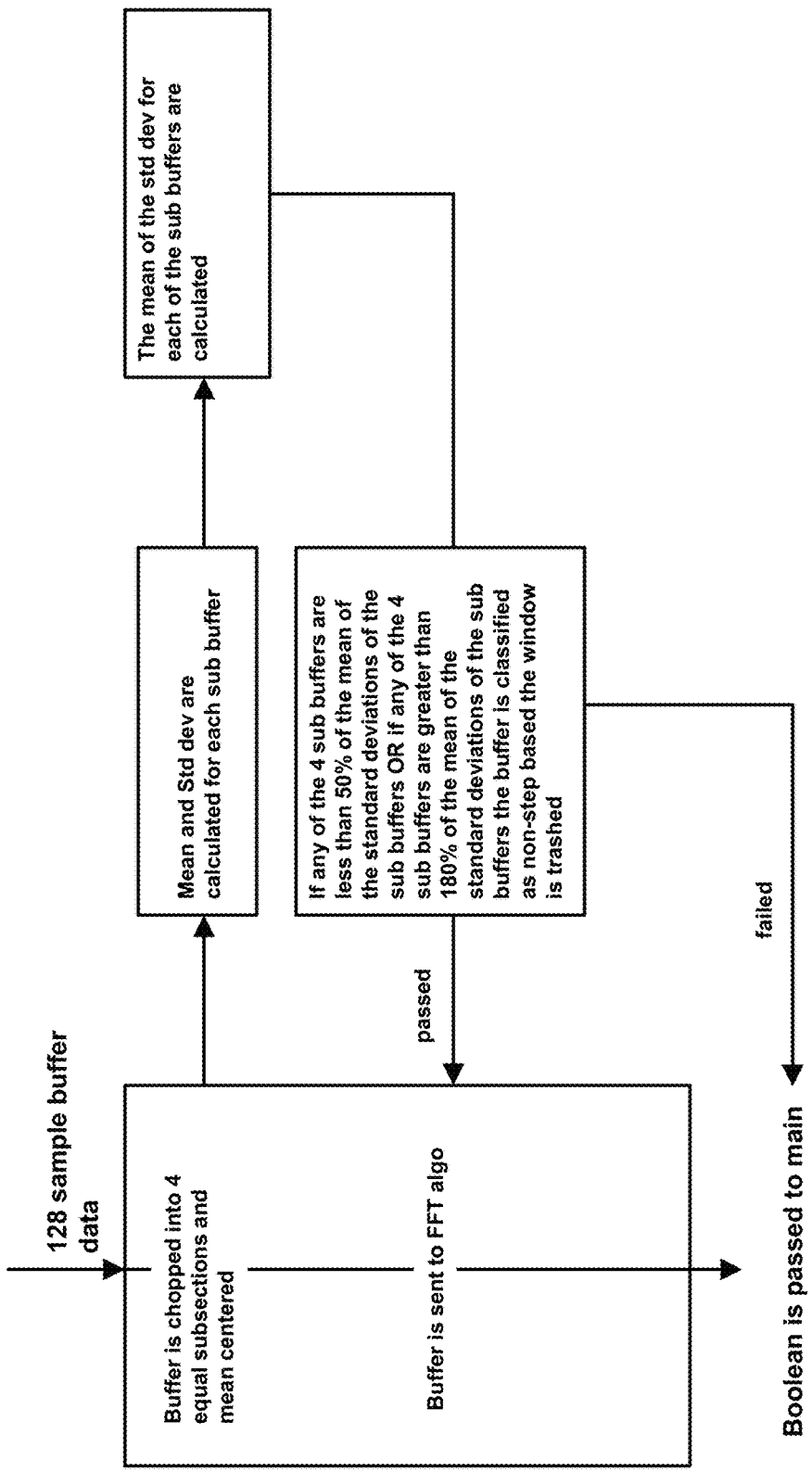
FIG. 6 shows an example flowchart that may be utilized to implement a classify function in accordance with one embodiment.
Figure 7A:
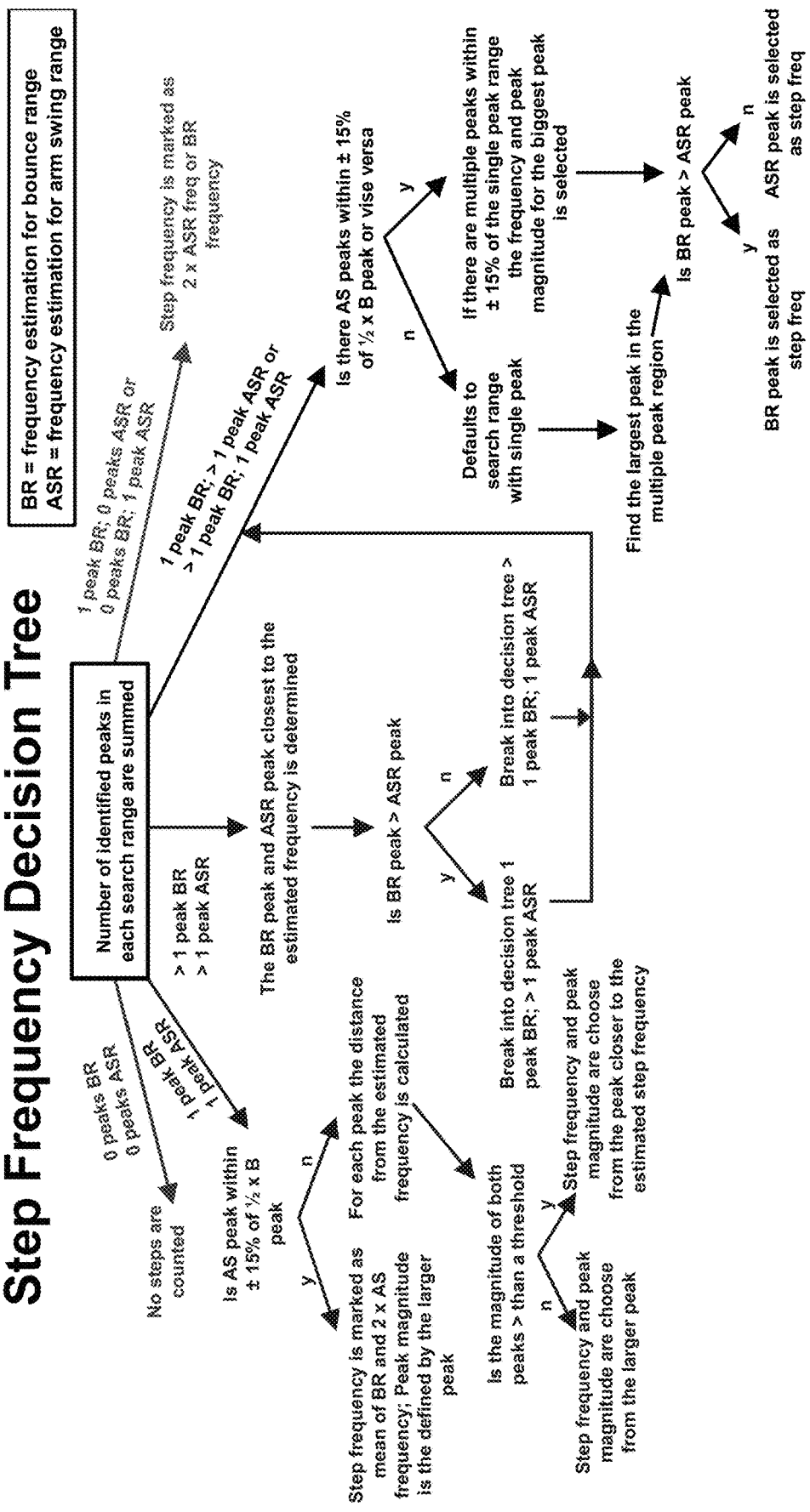
FIG. 7A shows an example flowchart that may be implemented to determine whether to utilize arm swing frequency or bounce frequency in accordance with one embodiment.
Figure 7B:
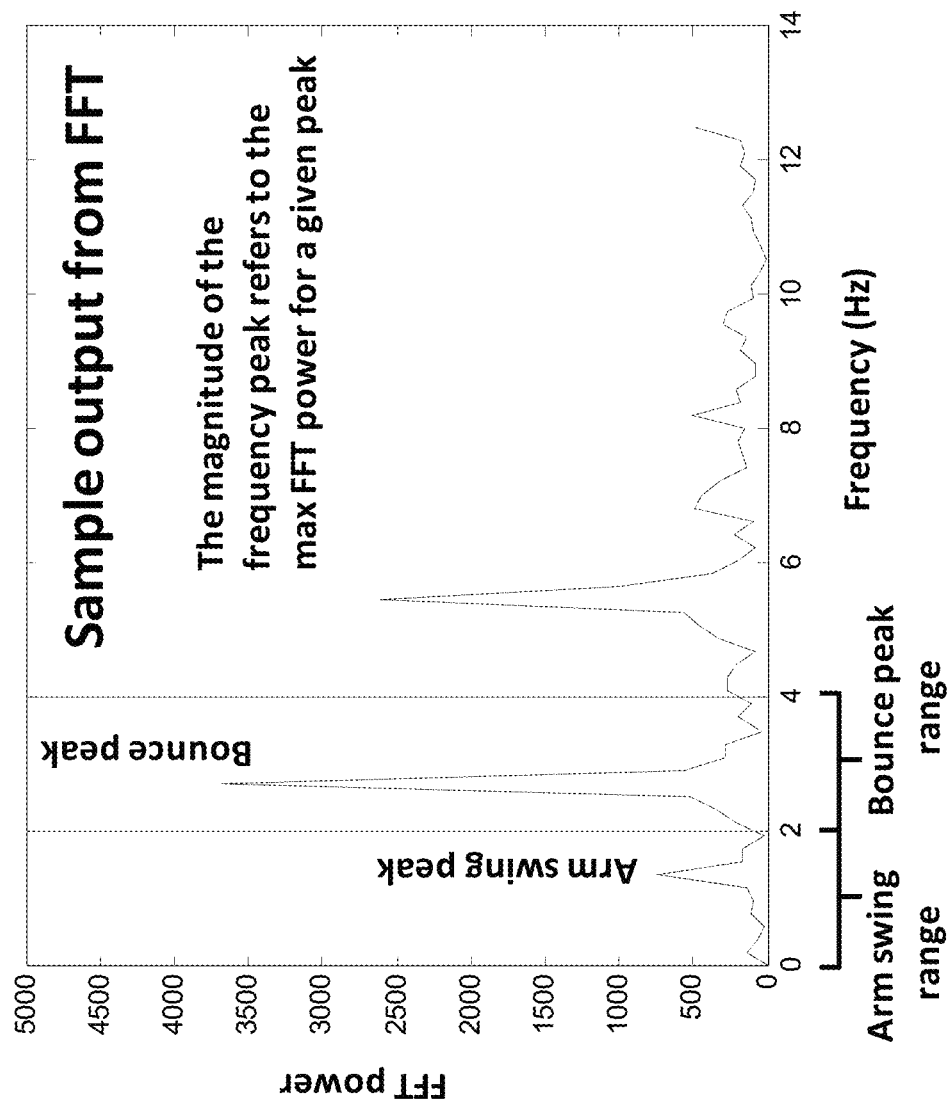
FIG. 7B shows an example in which the frequency off the bounce peak is generally twice the frequency of the arm swing peak.

FIGS. 3-9 show flowcharts of further embodiments that may be implemented in conjunction with, or independently of, each other as well as any other embodiments described herein. Generally:

FIG. 3 shows an example flowchart that may be utilized to quantify determine activity classification values in accordance with one embodiment;

FIG. 4 shows an example flowchart that may be utilized to quantify steps in accordance with one embodiment;

FIG. 5 shows an example flowchart that may estimate frequency and set up a frequency search range in accordance with one embodiment;

FIG. 6 shows an example flowchart that may be utilized to implement a classify function in accordance with one embodiment;

FIG. 7A shows an example flowchart that may be implemented to determine whether to utilize arm swing frequency or bounce frequency in accordance with one embodiment. As shown in FIG. 7A, the systems and methods may be implemented to select relevant frequency peaks out of the illustrative FFT output to determine a user's step frequency. In certain embodiments, step frequency may be used in the generation of a step count for the period of time represented by the FFT spectrum. As seen in FIG. 7B, the frequency off the bounce peak is generally twice the frequency of the arm swing peak. The peak magnitude indicates the relative strength of the frequency, and may be used as an indicator if a person is stepping.

Figure 9:
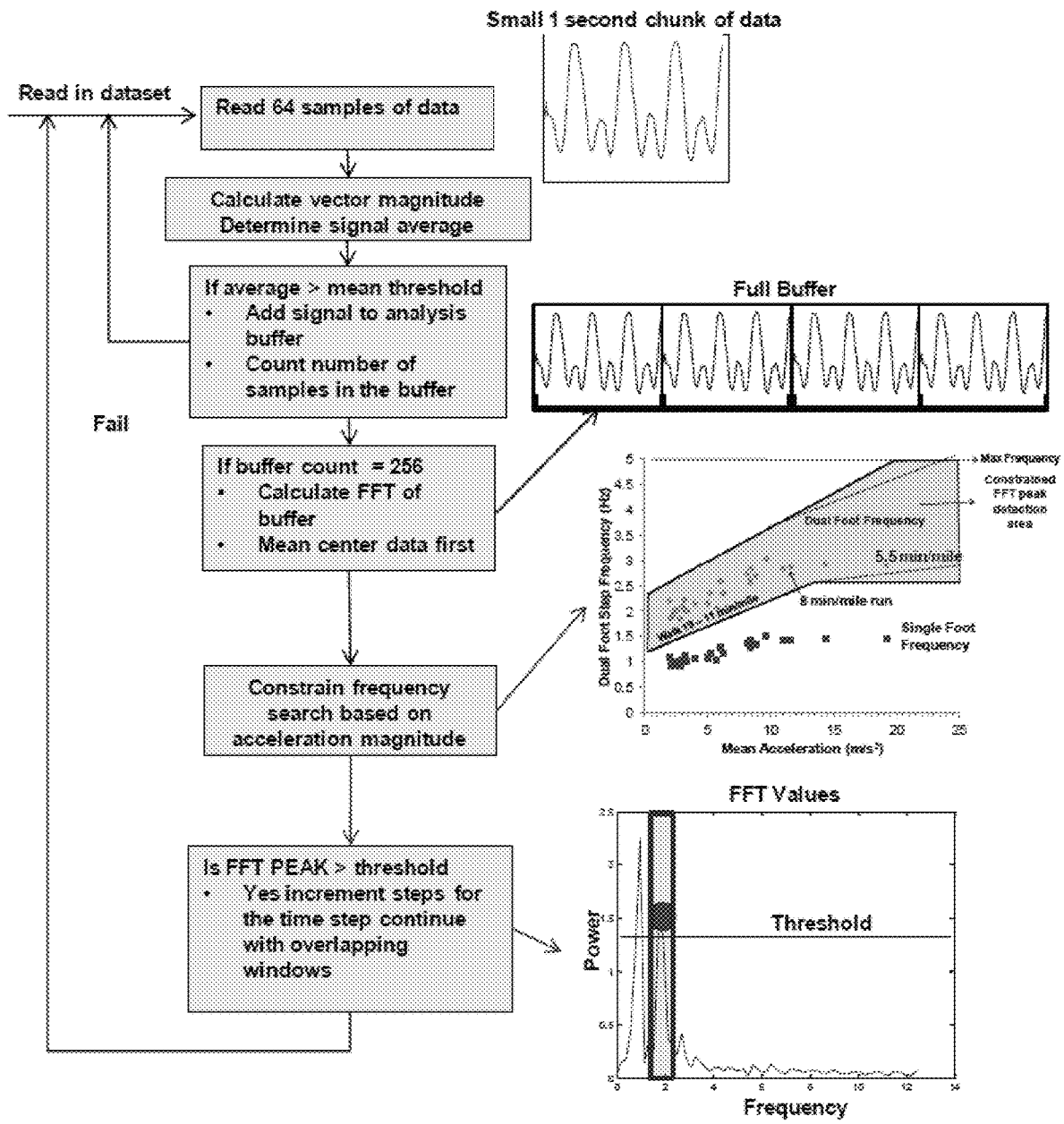
FIG. 9 shows an annotated flowchart of an embodiment of measuring activity of a user that may be implemented in accordance with yet another embodiment.

FIG. 8 shows an example flowchart that may be implemented to classify activity and determine speed in accordance with one embodiment; and FIG. 9 shows an annotated flowchart of an embodiment of measuring activity of a user that may be implemented in conjunction with, or independently of, other embodiments described herein. In this regard, aspects of FIG. 10 and the discussion below may overlap, be similar to, or otherwise comprise aspects of one or more embodiments described above. Various embodiments of step quantification systems and methods may relate to a low power, high fidelity, integer based step counter using a multi-tier technique. In one embodiment, motion, such as measured through an accelerometer, may be loaded into a multi-segment threshold based acceleration buffer. One or more system or methods may determine various portions of the data to determine if detected parameters are indicative of a specific action or activity. For example, peaks and/or valleys of accelerometer day may be measured to determine if they are large enough to be considered walking or running. In certain embodiments, utilizing multiple segments of the buffer may be utilized to ensure quick arm fluctuations are not misinterpreted by a device, and thus utilize limited processing power by conducting analysis of the data, such as for example, entering a frequency analysis mode. In this regard, certain embodiments may analyze data using Fourier transforms. Fourier transforms are a computationally expensive activity, therefore in certain embodiments, it may be preferable to not perform them when its determined to be unnecessary. Therefore, in one embodiment, contiguous segments (which may be 4 contiguous segments) must be assembled that have data (e.g., detected acceleration) above a threshold to be analyzed (such as, for example, by a frequency determination algorithm).

In certain embodiments, a mean acceleration of the buffer may be used to create a distinct narrow search range of the data (e.g., frequencies). The search range may relate the mean acceleration to an expected walking/running frequency. In one embodiment, if accelerations generate a frequency outside the frequency range that the accelerometry predicts, then certain systems and methods may not count these as steps. This may be utilized to insure data considered to be random noise (e.g. data with different frequency content but similar acceleration magnitudes) is not counted as a specific activity (e.g. running).

In certain embodiments, a threshold of the frequency power within the constrained search range may ensure that the frequency is not simply noise and that it is large enough to be considered an activity (such as, for example, walking or running).

In yet another embodiment, an overlapping window strategy may be utilized. For example, FFT windows may be analyzed in an overlapping fashion to make sure short term duration steps are counted.

As shown in FIG. 9, one or more systems or methods may confirm that a consistent number of samples (and/or duration of samples, such as for example 4 seconds) provide an acceptable range of consistent acceleration. In one embodiment, this may be performed by mean centering and then determining the mean of the absolute value of acceleration in each subsection (such as for example, each 1 second subsection of a 4 second buffer). Certain embodiments may determine if this absolute value mean greater than a threshold. If it is not greater than a threshold, the whole buffer (e.g., the entire 4 seconds) may be emptied and not analyzed until a valid series (e.g., 4 seconds of duration) of subsections is found with the correct acceleration magnitude. If this is the case, the buffer may be considered full and analysis (e.g., a Fourier transform) may be performed to determine the frequency content of the motion, such as for example, arm movement. The acceleration magnitude of the full buffer (e.g., 4 seconds) may also be used in determining constrained frequency search.

Correlation of acceleration data may be utilized to predict step frequency. In one embodiment, an absolute mean value of acceleration may be utilized in the correlation for predicting step frequency. A peak finding algorithm may analyze this region for the expected peak. If the peak exists and is above a final threshold, steps may be incremented. Otherwise, the data may be considered random noise. Varying amounts of window overlap can be used. In one embodiment, it may be 50% of the window, yet in another embodiment it may be based on time duration. In the illustrated example of FIG. 10, it may be set to 50% of the 4 second window size. In certain embodiments, window overlap is performed to ensure short bursts of movements on the order of half the full window size (i.e., 2 seconds) are not thrown out by the acceleration magnitude buffer. This overlap may be helpful for finding short bursts of activity among random movement and finding the first portion (e.g., 2 seconds) or last portion (e.g., a later two second increment) of a longer steady-state activity (e.g., a walk or run). At the end of all these steps when a valid frequency has been determined, steps are incremented by multiplying the frequency by the overlapping window time (e.g. 2 seconds).

Aspects of various embodiments may offer one or more advantages and/or benefits over the prior-known systems and methods. In certain embodiments, false positives are reduced or eliminated for short arm movements using the buffer filling strategy. Also, the constrained search for analysis (e.g. FFT) may assist in selecting the correct frequency relating the vertical bounce rather than the arm swing such that the correct walking frequency is obtained for two feet steps. In further embodiments, the overlapping of windows may allow for improved detection of short bursts of step activities. Finally, the frequency analysis may be performed on one combined channel of sensors so that arm rotation does not throw off detection and measurement of sensor outputs. Furthermore, by combining accelerometer channels, less analysis (e.g. fourier transform frequency analyses) may be performed. This may improve battery life.

III. Action Identification and Detection Using Templates

As described herein, activity classification may be performed by identifying various events and actions represented within data received from any number and type of sensors. Accordingly, activity tracking and monitoring may include determining whether one or more expected or known actions within an activity type has been performed and evaluating metrics associated with those actions. In one example, actions may correspond to a series of one or more low-level or granular events and may be detected using predefined action templates. Action templates may correspond to any desired level of granularity. In some examples, an event may correspond to acceleration of a user's foot in a particular direction or detection of foot contact or detection of foot launch (e.g., lifting a user's foot into the air). In other examples, an action may correspond to a group of such events, such as detecting that a user has taken a step to the right followed by a step to the left or detecting that a user has jumped while flicking his or her wrist. Using action templates, a system may automatically detect when a user has performed a particular activity or a particular motion expected during that activity. For example, if a user is playing basketball, detecting that the user has jumped while flicking his or her wrist may indicate that the user has taken a shot. In another example, detecting that a user has moved both feet outward while jumping followed by moving both feet inward while jumping may register as a user performing one repetition of a jumping jack exercise. A variety of other templates may be defined as desired to identify particular types of activities, actions or movements within types of activities.

Activity templates may be defined manually, semi-automatically and/or automatically. For example, a user may manually define the types of sensor events corresponding to an action, the ways in which the sensor events should be combined/organized, timing between the sensor events and the like. Alternatively or additionally, action templates may be automatically defined based on user performance of the action. The system may be configured to record a user's performance of an action and automatically build a template based on the types of sensor events, timing of the sensor events and other combinations of the sensor events detected during the performance of the action. The user may indicate that an action was performed within a time window and have the system identify the corresponding events and constraints. In yet other examples, a system may automatically identify actions based on recurring patterns in an event stream without user specification of the action or that the action has been performed.

Events may be defined/represented in a variety of manners and may relate to a multiple types of information. In one example, an event may correspond to multi-element tuples comprised of a label (e.g., an event type) and/or measurements/values. In a particular example, an event may correspond to a syntax such as: <person XYZ's heart rate, 4:34:17.623PM GMT, 86 beats per minute>. Other example events may include: <ground air temperature, 4:34:17.623PM GMT, 45° 31' 25" N, 122° 40' 30" W, 67° F.>and/or <left heel pressure, 4:34:17.623PM GMT, 400.23 kPa>. However, events may adhere to other varying syntaxes (using either a predefined structure or mark-up labels) and include additional or alternative information as desired or needed. Events may be used to convey multiple types of information including physical environment characteristics (e.g., humidity, temperature, air pressure), social environment characteristics (e.g., what people are saying), user physiology characteristics (e.g., movement, heart rate, blood lactate level), and/or user behavior (e.g., cell phone usage, amount of active time, amount of inactive time, etc.). In one example, event streams may include simple events such as threshold value crossings, sums, and local extrema as well as computationally more complex events, including local extrema in the derivative values of composite readings values and semantically richer events such as "steps" (which may involve a dynamic threshold applied to combinations of pressure sensors). Events may include a variety of information including a reference timestamp of when the event occurred (or was computed), a timestamp indicating when the event generation process was initiated (which may apply to events triggered by other events (e.g., complex events triggered by other events)), and an event value (measurement). Each of these pieces of event information may be used to help score or evaluate the event to determine whether the event corresponds to a match with a template. In some arrangements, an event defined in a first template may correspond to (e.g., require) matching of a second template.

According to one or more arrangements, an activity processing device or system configured to identify actions performed by the user may also include one or more sensors. Accordingly, events may be detected by the activity processing device itself based on various sensor data. For example, the activity processing device may be used to track a user's arm motion if the device is hand-held or worn on the user's arm. Additionally or alternatively, the activity processing device may provide options to the user to manually mark or generate events. For example, the user may be able to manually enter when he or she lifted their right foot, run a predefined distance, squatted and the like and/or combinations thereof. In a particular example, the user may tap or otherwise interact with the activity processing device to generate and mark such events.

Figure 17:
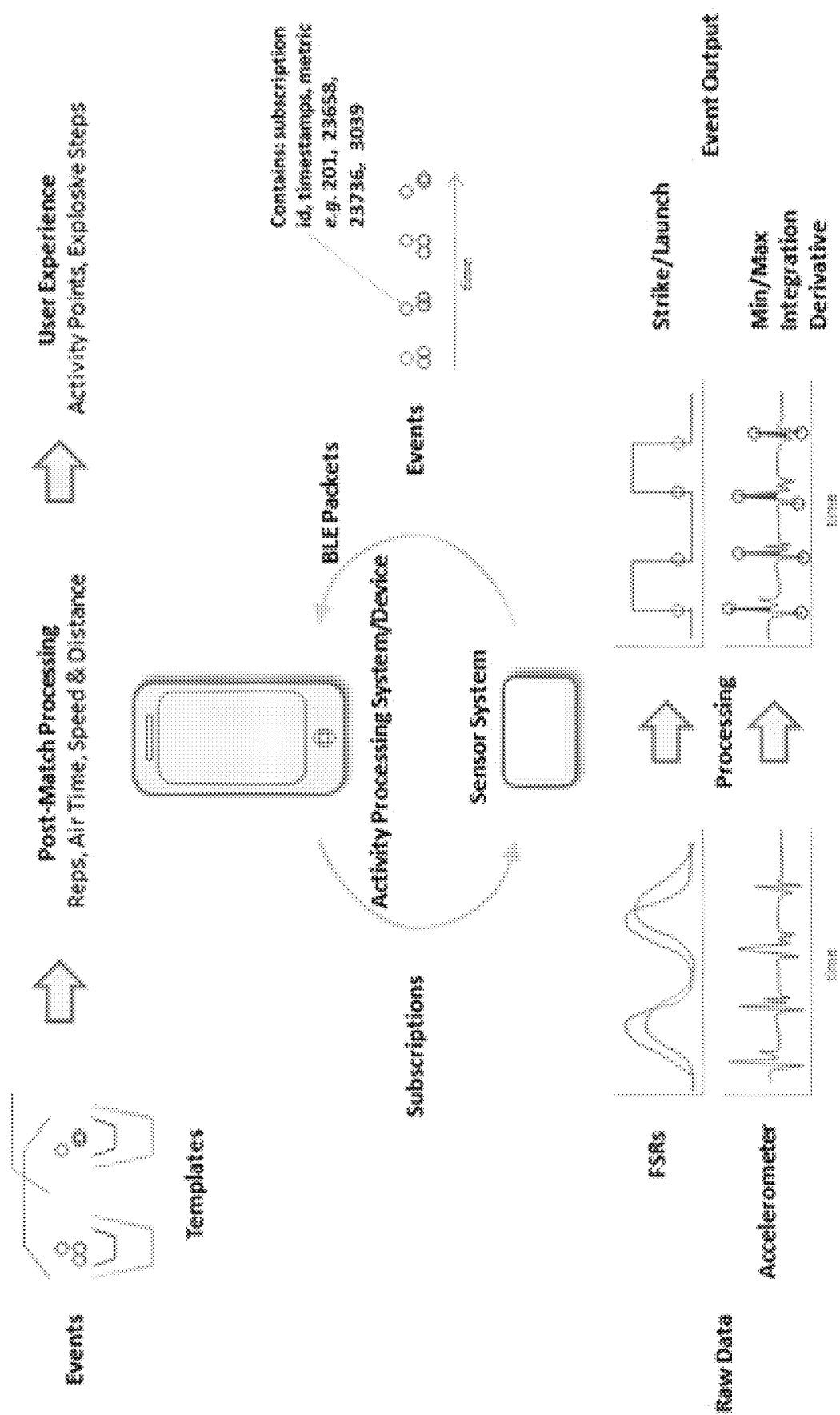
FIG. 17 is another example data flow diagram for activity processing.

FIG. 17 illustrates an example system diagram in which an activity processing device or system interfaces with a sensor system to detect user actions. The sensor system may be physically separate and distinct from the activity processing device and may communicate with the activity processing device through wired or wireless communication. In one or more examples, the sensor system may correspond to a single sensor, a group of sensors, single type of sensor, multiple different types of sensors and the like and with or without processing capabilities. In a particular example, the sensor system may correspond to sensor system 200 or 260 of FIGS. 2A and 2C, respectively, and/or a sensor assembly of device 226 of FIG. 2B. Additionally, as illustrated, the sensor system may be configured to perform initial processing of raw sensor data to detect various granular events. The sensor system may also manage data subscriptions that are used at any particular time, as is further described in detail herein.

The events may then be passed to the activity processing system where the events are compared to various templates to determine whether an action has been performed. Moreover, the activity processing system may be configured to perform post-match processing which may include determining various activity metrics such as repetitions, air-time, speed, distance and the like. The activity processing system may correspond to any number or type of computing system including device 138 or device 226, gaming systems, servers, cloud systems, mobile devices (e.g., smartphones, cell phones, etc.), desktop computing devices, laptop computing devices, tablet computers, wearable activity monitoring devices and the like. Additionally or alternatively, the activity processing system and the sensor system may correspond to and/or be integrated in the same device.

Figure 10:
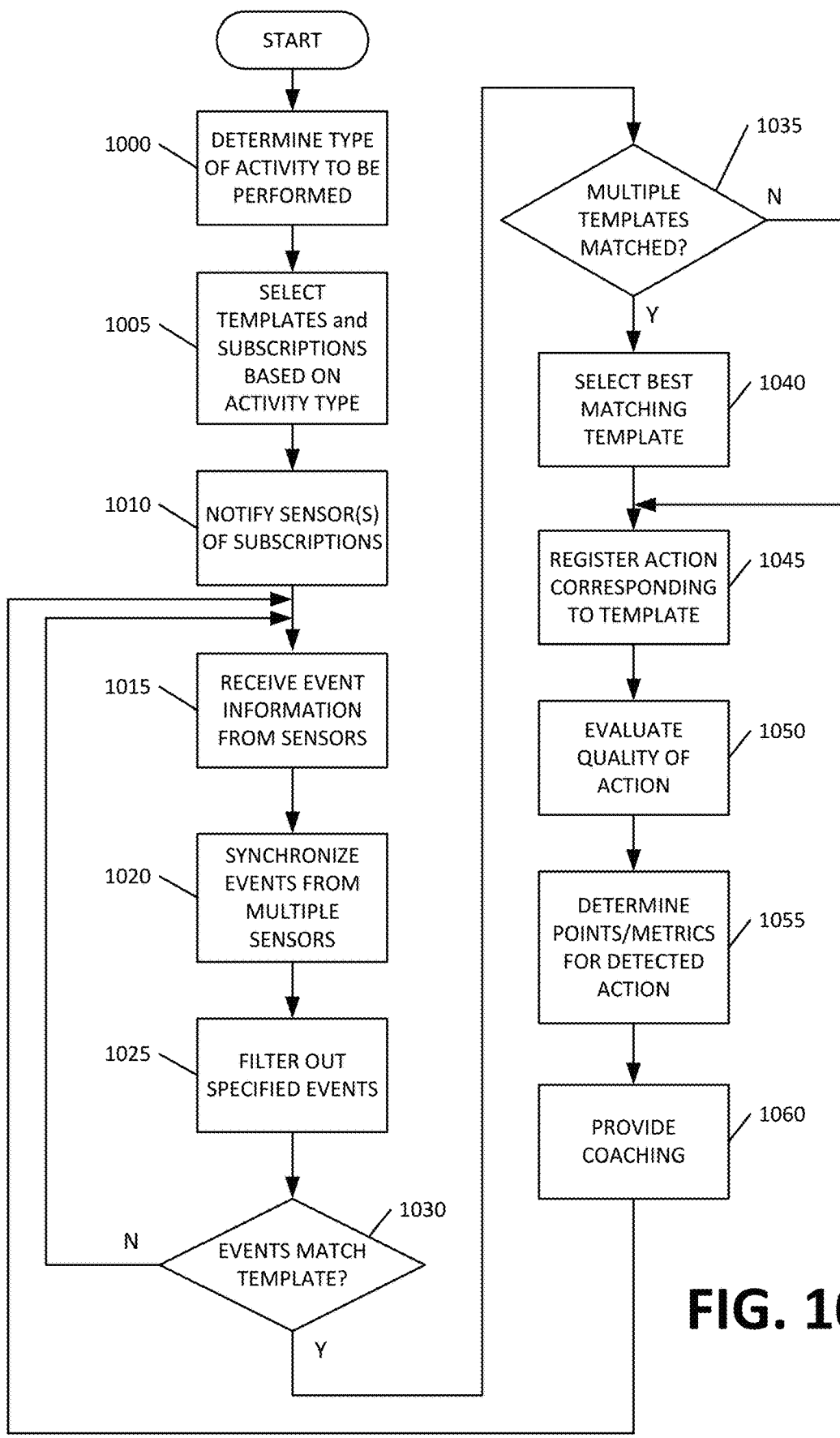
FIG. 10 is a flowchart illustrating an example process for matching user activity events to one or more action templates.

FIG. 10 illustrates an example process by which events may be detected and compared to predefined action templates to identify user motions during physical activity. In step 1000, an activity processing device or system may determine a type of physical activity to be performed by the user. The physical activity may be a type of sport, a drill or test, an exercise, a physical activity game and the like. Different types of physical activity may correspond to different sets, arrangements, categories and/or types of physical movements and actions. In one example, the type of physical activity may be determined based on receiving a user selection of the physical activity type. Alternatively or additionally, the system may determine the type of physical activity by comparing detected activity signals (e.g., received from sensors) with predefined rules corresponding to different types of physical activity as described herein. The activity signals may be received from various sensors including wrist-borne devices, head-worn devices, chest-worn devices and/or shoe-borne devices. In some examples, a first set of predefined rules for basketball may include a certain combination and type of wrist and arm actions combined with detecting a user walking. A second set of predefined rules may be defined for jogging based on a first threshold pace of foot contact events (e.g., above the first threshold pace). Yet another set of predefined rules may be defined for walking based on a second threshold pace of foot contact events (e.g., below the second threshold pace). In yet other examples, a combination of user selection and automated detection may be used such that a user may select a broad category of activity such as running and the automated detection may be used to determine a sub-category of activity such as jogging or sprinting.

In step 1005, the system may select one or more predefined action templates and sensor subscriptions based on the determined type of activity to be or being performed by the user. Action templates may be used to identify motions or actions that a user may perform during the determined type of activity. Accordingly, different sets of one or more action templates may be defined for different types of activities. For example, a first set of action templates defined for basketball may include dribbling, walking, running, backpedaling, side shuffling, pivoting, jumping, shooting a basketball, boxing out, performing a slam dunk, sprinting and the like. A second set of action templates defined for soccer may include kicking a ball to make a shot, dribbling, stealing, heading the ball and the like. In one example, the number of templates may range from 1-100. In some examples, a particular type of activity may include 50-60 templates. In still other examples, a type of activity may correspond to 20-30 templates. Any number of templates may be defined as appropriate for a type of activity. In some examples, the number of templates may be selected based on an amount of battery life available, a maximum battery capacity, a processing speed of the activity processing device or system, a latency between a sensor system and the activity processing device or system and the like and/or combinations thereof. Accordingly, if the activity processing system or device has low available battery life, the system or device may select a number of templates that allows the device or system to last for a predefined amount of time. In other examples, the number of templates selected may be limited by the processing speed of the activity processing device or system. This limitation may insure that the device or system is able to process data against all of the selected templates at a given rate. In still other examples, the templates may be manually selected by a user rather than being selected by the system.

According to some aspects, templates may be prioritized such that high priority templates are first used to match with events while lower priority templates may be used if the events do not match any of the high priority templates. The use of a catch-all template may allow users to determine metrics associated with movement or other events that might not be matched with a predefined action template. The data falling into the catch-all template may also be aggregated for use in improving sensor readings or metric calculations in one or more devices. Priority may be defined by a likelihood of a corresponding action being performed during a type of activity, by a likelihood of a corresponding action being performed by the specific user, based on a subjective level of importance of the action, based on user specification (e.g., manual prioritizations), popularity of an action (e.g., occurrence of the action) within a community of users and the like and/or combinations thereof.

In step 1010, the activity processing system may notify the sensor system of the selected subscription(s). The notification to the sensor system may be configured to cause the sensor system to configure monitoring functions to receive sensor data from the sensors specified in the subscription while not monitoring or receiving sensor data from sensors not specified in the subscription. Additionally or alternatively, the notification may cause the sensor system to process sensor data into one or more events based on subscription parameters and return only those events that match the specified parameter. In yet other examples, the notification may cause the sensor system to configure what data and/or events are to be returned to the activity processing system.

According to some arrangements, sensor subscriptions are configured to identify the types of information to be provided by a sensor system. In some examples, the sensor system may be configured to select the sensors to monitor for data based on the subscriptions. For example, if a sensor system includes 4 force sensitive resistive sensors and an accelerometer, the subscriptions may specify which of those 5 sensors (7 if the accelerometer includes 3 axes of sensing) are monitored for sensor data. In another example, subscriptions may specify monitoring, by the sensor system, sensor data from a right shoe accelerometer but not a left shoe accelerometer. In yet another example, a subscription may include monitoring data from a wrist-worn sensor but not a heart rate sensor. Additionally or alternatively, the sensor subscriptions may control the sensor system to turn on or off certain sensors so as not to conserve power. Thus, if sensor data from an accelerometer is not required or subscribed to, the accelerometer may be turned off Subscriptions may also control types and levels of processing performed by the sensor system. For example, a subscription may specify sensor thresholds to adjust the sensitivity of a sensor system's event detection process. Thus, in some activities, the sensor system may be instructed to identify events corresponding to all force peaks above a first specified threshold. For other activities, the sensor system may be instructed to identify events for all force peaks above a second specified threshold. Still further, subscriptions may be used to control the types and/or amounts of data and events communicated to the activity processing system. Accordingly, irrespective of which sensors are active, what sensors are being monitored and/or what events are generated/detected, the sensor system may also independently control what data (e.g., raw sensor data or events) are transmitted to the activity processing system. Thus, while a sensor system may detect all events corresponding to acceleration along the z-axis higher than a first specified threshold, the subscription may request transmission of only z-axis acceleration events higher than a second specified threshold higher than the first specified threshold. Use of different sensor subscriptions may help a sensor system to conserve power and/or communication bandwidth if some sensor readings are not needed for a particular activity. Accordingly, different activities and activity types may use different sensor subscriptions.

Example subscriptions may include force sensitive resistance data from one or more force sensitive resistors, acceleration data from one or more accelerometers, summation information over multiple sensors (e.g., summation of acceleration data, summation of force resistance data over one or more sensors, etc.), pressure maps, mean centered data, gravity adjusted sensor data, force sensitive resistance derivatives, acceleration derivatives, environmental sensor data (e.g., temperature, weather, terrain, etc.), social information (e.g., identification of other users joining in the activity or within a predefined proximity, data regarding other user's activity performances, etc.) and the like and/or combinations thereof. In some examples, a single subscription may correspond to a summation of data from multiple sensors. For example, if a template calls for a shift in force to the forefoot region of a user's foot, a single subscription may correspond to a summation of forces of all sensors in the forefoot region. Alternatively, force data for each of the forefoot force sensors may correspond to a distinct subscription.

In accordance with the specified subscriptions, in step 1015, the activity processing system may receive event information from the sensor system. In one example, the event information may be received from a wrist worn device such as device 226, a shoe based sensor such as shoe sensor system 202 and/or a sensor resident in the activity processing system itself. Additionally, the event information may be generated and filtered by a sensor system based on subscription parameters. The various sensor systems may be configured to pre-process raw sensor signal data to identify predefined events in order to reduce the frequency with which the sensor systems and/or activity processing system transmit and receive data. Accordingly, the activity processing system might only receive sensor data when events are detected and/or for events that match subscription parameters. Alternatively, raw sensor signals may be received by and processed by the activity processing system to identify events, if desired.

Actions may be defined based on a combination or set of sensor events. For example, running may correspond to a series and pace of foot contact times and launch times. In another example, kicking a ball may be defined by a foot launch event, followed by foot acceleration along a specified axis and a subsequent slowing or change in acceleration (e.g., when the user's foot strikes the ball). Accordingly, the sensor systems may be configured to identify individual events based on predefined rules as described herein while the activity processing system may be configured to identify user actions corresponding to combinations of one or more individual events detected by the sensor system.

In step 1020, the system may further synchronize the sensor events to account for deviations in sensor clocks and transmission times. In particular arrangements, the system may measure the required transmission time between each of the sensors and the activity processing system and subsequently use the measured transmission time to adjust a time associated with each of the detected sensor events. Additionally or alternatively, synchronization may include temporally sorting the events received. In some examples, event data might not be received in an order in which the events were detected. Accordingly, the system may pre-process the event data to order the events according to the time at which they were detected.

Optionally, in step 1025, the system may evaluate the event information received and apply one or more filters to remove various types of events. According to some arrangements, disqualifying events or rules may be defined such that events are filtered from the event stream to be processed in identifying user performed actions. In one example, the system may receive notification of two feet launch events from a shoe sensor without an intervening foot contact event. Such an occurrence would indicate that the user had jumped twice without landing after the first jump. In such an example, the system may disqualify or remove at least the second foot launch event. Additionally, the system may also disqualify the first foot launch event. In another example, the system may filter out events based on an amount of time between the event time stamps. Accordingly, if an amount of time between a foot launch event (e.g., detected by a first shoe sensor) and a foot contact or strike event (e.g., detected by the same first shoe sensor) is above a specified threshold, the foot launch and foot strike events may be filtered out of the event data. The specified threshold may be set to a maximum possible amount of air time that is humanly possible. In still another example, if a user is performing a jumping jack exercise, the system might not register (e.g., identify) that a repetition has been performed if an amount of time between the foot contact time and the foot launch time is too great. Filters may include one or more filter templates comprising arrangements of one or more events. Upon matching the filter templates, the matching events may be removed from the event stream (e.g., buffer) and/or processing.

As discussed herein, filters may also be used to remove certain events that are not applicable to the determined type of activity. For example, if the determined type of activity is running, foot pitch measurements or head movements might not be relevant to determining metrics for the running activity. Accordingly, such sensor events may be filtered out from the events used to evaluate user actions. Filters may be selected depending on the type of activity to be performed by the user. Accordingly, the types of filters applied to event information may differ depending on the type of activity to be performed. For example, while head movements might not be relevant to determining metrics or actions for running, head movements may be relevant and used to detect juke movements in basketball. In some examples, information regarding the selected filters may be sent to the one or more sensor systems being used such that the sensor systems do not detect or filter out sensor events in accordance with the filters. Accordingly, the activity processing system might not need to perform filtering functions if the sensor systems have previously performed such processing.

In still other examples, filtering may be performed based on results from multiple sensors. Thus, if multiple sensors are used, sensor events may be filtered out if data from the other sensors do not provide sufficient confirmation or corroboration of the event or action. In an example, an accelerometer of a shoe may register a foot launch event based on acceleration detected along a z-axis. However, if a pressure sensor of the shoe indicates that a pressure differential at the time the foot launch event was detected is below a specified threshold (e.g., a pressure differential threshold corresponding to a foot launch event), an activity processing system may filter out the foot launch event received from the accelerometer. In one or more arrangements, a of the sensors configured to detect a particular type of event (e.g., foot contact, foot launch, wrist flick, head tilt, change in pressure profile, etc.) may be required to detect the event for the event data to be retained. If less than a majority of the configured sensors detects the event, the event data from those sensors that detected the event may be filtered out.

In other arrangements, certain sensors may be given more weight or confidence than other sensors. Accordingly, the amount of corroboration needed for each sensor may differ depending on the weight or reliability of the sensor. For example, a shoe pressure sensor may be more reliable in detecting foot launch and foot strike events. Accordingly, even if one or more other sensors does not register a foot launch or foot strike event, the foot launch or foot strike event detected by the pressure sensor might not be filtered. In another example, if the other sensors detected a foot launch or foot strike event, but the event is not detected by the shoe pressure sensor, the event may be filtered out regardless of the number of other sensors that detected the event. The reliability or confidence in a particular sensor or set of sensors may vary depending on the type of event. Accordingly, while the shoe pressure sensor may be deemed more reliable in detecting foot launch or foot strike events, the shoe pressure sensor might not be afforded the same amount of confidence in detecting foot movement in longitudinal and lateral directions. Thus, different filtering rules may be applied depending on type of event as well as type of sensor (e.g., location at which the sensor is located, sensor technology and the like). The above filtering rules, parameters, weights and other factors may be specified within a filter template or separately from the templates. Accordingly, in some cases, each filter template may weigh sensor confidence differently.

As noted, the above filtering process of step 1025 is optional and might not performed or used in certain configurations or systems. Other types of filtering or event exclusion processing may be used instead of or in addition to the filtering described in step 1025. An example of exclusion event processing is described in further detail herein.

In step 1030, the activity processing system may determine whether the received events match one or more predefined action templates. In one example, predefined action templates may be compared to a continuous stream of events received from the sensor system. Alternatively or additionally, the predefined action templates may be compared to a sliding window of event data. For example, each set of X samples may be compared to the predefined action templates. The set of X samples may then be incremented by a predefined number of samples (e.g., 1 sample, 2 samples, 5 samples, 100 samples, etc.) and the new set of X samples may then be compared to the templates. Samples may be defined by time, events, data units and the like. In an example, the sample window may be 2 seconds. A template matching process is described in further detail below with respect to FIGS. 11 and 12.

Some activities may include multiple templates. Accordingly, in some arrangements, a single combination of detected events may match multiple templates. Thus, in step 1035, the system may determine whether multiple templates were matched in the matching process of step 1030. If multiple templates are matched, the system may select one of the matching templates to determine the action corresponding to the combination of events in step 1040. Selecting one of the multiple matching templates may be performed according to various algorithms and methods. In one example, selection may include determining a strongest or highest level of match between the combination of events and each of the templates. In another example, selection may include determining a likelihood of each of the actions corresponding to the matching templates given one or more other events or actions detected within a predefined temporal proximity. For instance, if a wrist snapping event and a foot strike event are determined to match both a basketball shooting action and a basketball dribbling action, selection of one of the two actions may be based on surrounding actions or events. In a particular example, if the wrist snapping and foot strike events are preceded by a jumping action (e.g., detecting foot launch events of both feet at around the same time), the system may select the basketball shooting action as the matched template since a user is unlikely to jump while dribbling. Various other selection methodologies may be used.

If the combination of events does not match multiple templates or upon selecting a best matching template, the activity processing system may then register an action (or detection of an action) corresponding to the matching template in step 1045. For example, each template may be associated with a particular action such as slam dunking, juking, shooting a basketball, sprinting, jogging, walking, performing a lateral hop, kicking a ball, heading a ball, throwing a ball, and the like. Registering an action may include storing the action in a database or log of actions performed by the user, conveying a message to the user notifying them of the action performed, transmitting the detection of the action to one or more devices including remote activity tracking systems and the like and/or combinations thereof.

Furthermore, in some examples, the activity processing system may evaluate a quality of the registered action in step 1050. The quality of the action may be determined in a variety of ways including by determining the strength of the match between the combination of events and the action template and/or determining whether optional states in a template have been matched. For example, optional or bonus states might not be required to identify the combination of events as a match with a template, but matching those optional or bonus events may indicate a higher quality of performance. A quality scale may be defined based on a linear or non-linear relationship with the strength of the match. In one example, if a user's window of events matches within 7-10% of a template having a maximum tolerance of 10%, the quality of the user's action may be defined as "low." However, if the user's level of match is within 3-6.99%, the user's action quality may be defined as "medium," while a level of match within 0-2.99% may be defined as "high." In some examples, a further level of quality such as "perfect" may be defined for 0% deviation from a corresponding template. Quality may be denoted by a numeric value (e.g., scale of 1-10), letter grade (e.g., A, B, C, D, etc.), color (e.g., red, yellow, green), sound (e.g., boos, mild cheers, wild cheering), level or type of haptic feedback (stronger buzzing indicates lower quality or vice versa) and the like.

In some examples, quality analysis may include weighing certain portions of the template higher or lower than other portions of the template. Accordingly, a user who deviates during a more highly valued portion of the template may be assigned a lower action quality score than a user who deviates during less valued portions of the template. In a particular example, a kicking action in soccer may comprise a foot lift event, a foot forward event and a ball strike event. In this example, the ball strike event may be more highly valued since it may determine a force with which the ball was struck. Accordingly, if a first user matches the foot lift event and the foot forward event perfectly but deviates from the ball strike event by 25%, the quality of the user's ball kicking action may be "medium." In contrast, if a second user matches the foot lift event and the foot forward event with 90% accuracy (deviation of 10%) but matches the ball strike event perfectly, the quality of the second user's ball kicking action may be "high." Various other parameters of an action or template may also be weighted. For example, timing may be given higher weight for some events.

In step 1055, the activity processing system may determine metrics associated with the performance of the action. For example, the metric may be a count of the number of actions of a particular type performed, a distance, pace, force, height, speed and the like of the action, streaks (e.g., a number of consecutive actions of the same type performed) and the like and/or combinations thereof. Such metrics may be determined from the action information and event data corresponding thereto according to various algorithms and formulas.

In step 1060, the activity processing may optionally provide coaching to the user. Coaching may include instructions or recommendations for improving the user's performance of the detected action. The user might only receive coaching if the quality of the user's performance of the action is below a specified threshold. Coaching may be event-specific or event type-specific. For example, coaching may be generated based on individual events or groups of events where the user did not match the template to specified level (e.g., 95%, 90%, 85%, 70%, etc.) or the user's performance did not match optional or bonus events. Thus, the system may recommend improving the one or more events having an insufficient match level with the template and/or performing the optional or bonus events. For example, if the detected action corresponds to kicking a soccer ball and the user's foot forward acceleration event is a predefined percentage below an expected level, the system may recommend that the user increase his foot forward acceleration by the predefined percentage. In another example, if the detected action corresponds to performing squats, and a heel weight event indicates that amount of weight shifted to the user's heel is below an expected value, the system may recommend shifting more weight to the user's heel. In the same example, if an amount of weight shifted to the user's heel is above an expected value, the system may recommend reducing the amount of weight shifted. Coaching may also be generated based on other parameters and factors including weather, social factors (e.g., number of people performing same types of activity or actions or an average level of match of others performing the same or a similar action or activity), terrain and the like. Various other recommendations and instructions may be provided.

In some embodiments, different templates may be used depending on a dominant hand or foot of the user. For example, if a user's left foot is his dominant foot, then a jumping, lunging or other action template that is configured to detect the corresponding actions based on left foot sensor readings. For example, the left-foot based templates may give preference to sensor readings from a left shoe sensor. In another example, left-foot based templates may define a step or other event or action based on a triggering event by the left foot rather than the right foot. Templates may further be specific to a user, to a particular type of terrain, a time of day, a type of weather condition and the like.

Figure 11:
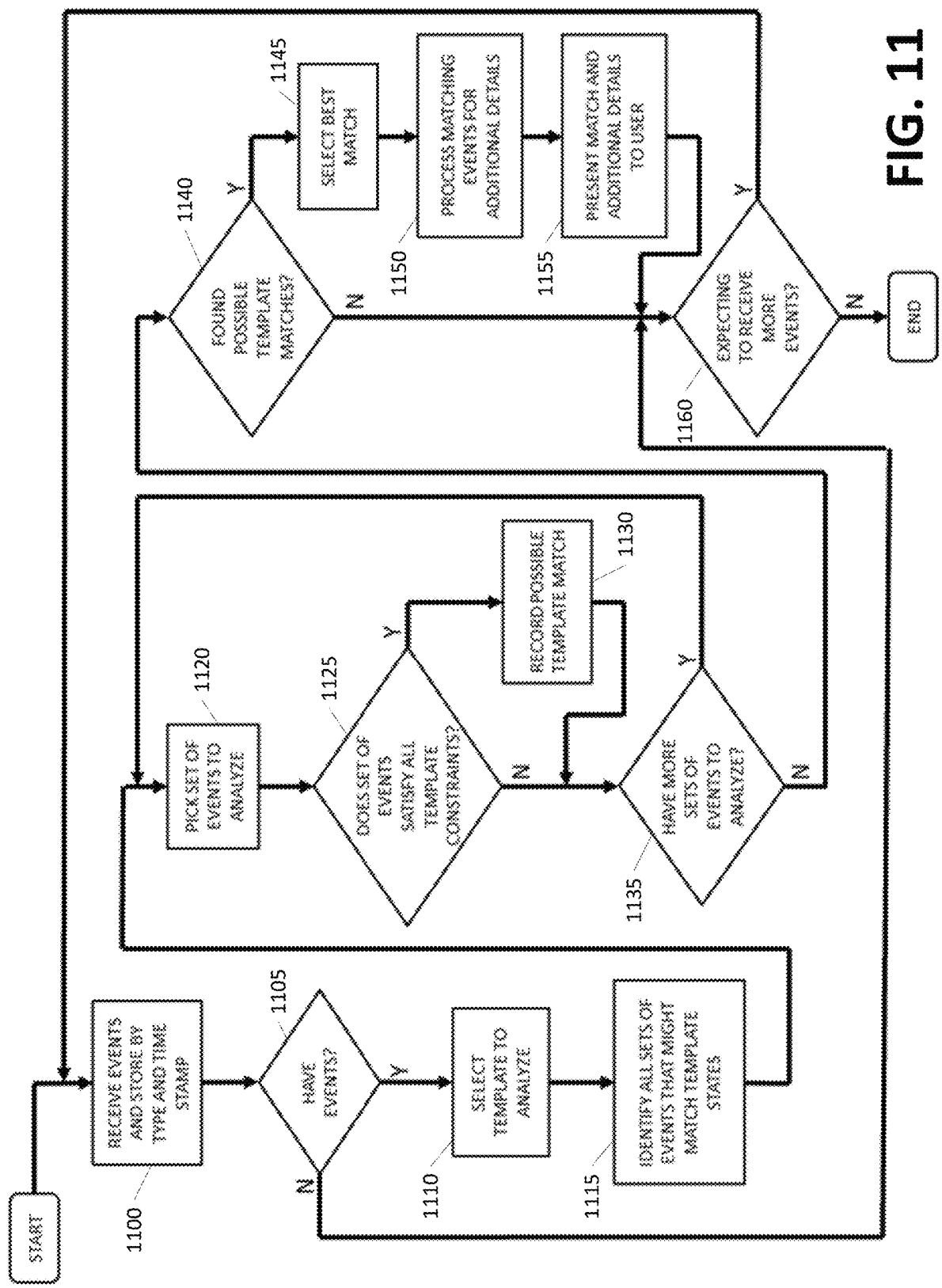
FIG. 11 is a flowchart illustrating an example template matching process.

FIG. 11 illustrates an example template matching process that may be used to determine whether detected events match an action template. The process may be performed for each of multiple action templates as needed or desired. In step 1100, an activity processing system may receive multiple events from one or more event sources and store those events by event type and time stamp. The event sources may include internal sensors, user input, external sensors and the like. In step 1105, the system may determine whether events are stored, received or otherwise available for template matching analysis. If not, the system may proceed to step 1160, where, if more events are expected, the system will return to step 1100. Otherwise, the system may end the process. In some instances, the system may determine if a sufficient amount of events is stored or has been received in step 1105. In an example embodiment, a sufficient amount may correspond to a guiding threshold amount of data for analysis. In another example embodiment, a sufficient amount may correspond to having at least a required or threshold amount of data for analysis. In either of these or other embodiments, a sufficient amount may be defined relative to or based on a number of events in a template. If the system determines that events are stored (or that a sufficient or requisite amount of events are stored or have been received), the system may subsequently select a template to evaluate against the received events in step 1110. Templates may be selected based on a type of activity being performed by the user and/or a priority of templates.

In step 1115, the system may identify sets of events that may match the states defined in the template. In some examples, the activity processing system may identify all sets of events that match the states among all available event data. In other examples, the activity processing system might only identify sets of events within a predefined amount of time (e.g., last 5 minutes, last 2 minutes, last 30 seconds, last 5 seconds, etc.). A template state may refer to required or preferred event types defined in the template. In one example, the received events and the template states may be matched based on a specified event type. The received events and the template states may both include labels specifying an event type. Accordingly, these parameters may be compared to determine whether an event type match exists.

In step 1120, the system may select one of the sets of events to analyze for template matching. The system may select one of the sets of events based on selected parameters, such as a recency or age of the newest or oldest event in the set, types of events, combinations of event ages (e.g., oldest event of a first type and a newest event of a second type), randomly, or based on other rules. In step 1125, the system may determine whether the set of events satisfies a requisite number (e.g., 25%, 50%, 75%, 80%, 90%, 100%) of template constraints for each of the template states. Constraints may be similar to the filters described with respect to FIG. 10, but may differ in the scope of how they are applied. For example, constraints may be defined within a template state and might only apply when evaluating that template state. in contrast, a filter may be applied independently of other template state to remove specified candidate events from consideration. Various types of constraints may be defined, including time constraints, value constraints, duration constraints and the like and/or combinations thereof. Additionally, constraints may be categorized into relative constraints and non-relative constraints. Relative constraints may relate to (e.g., define one or more required, preferred or desired relationship with) other template states, events matching other template states, aggregate statistics about prior events, and the like. Non-relative constraints may be evaluated solely based on the single event. For example, a non-relative constraint may define a required, recommended and/or preferred characteristic of a corresponding template state that is independent of other template states. A foot contact template state may include a constraint that a foot contact event has a duration of at least 100 milliseconds. Accordingly, foot contact candidate events may match the state by having a duration of at least 100 milliseconds without consideration of other template states in the template.

As noted, template states and constraints may refer to statistics about prior events, prior activity performances, statistics or metrics for matched events/states and the like. For example, a template state constraint may require that a foot contact duration be within 10% of an average of foot contact duration of one or more previously matched foot contact events for a particular template or activity type. Using previously collected metrics and statistics, the activity processing system may thus provide dynamic calibration and/or filtering based on a user's previous performance. Since different users may exhibit different gaits and other activity performance characteristics, the user's statistics and metrics may be more accurate in calibrating event and action detection to the individual user.

Time constraints may include strict, loose and relative ordering requirements for a particular event. For example, strict temporal ordering may include requiring that event B occur between events A and C. Loose temporal ordering may include a requirement that event A and B occur within 100 milliseconds of each other while relative temporal ordering may include a requirement that event B occur mid-way between the occurrences of events A and C, plus or minus 10% of the duration between the occurrences of events A and C.

Value constraints may include requirements for a signal or event value (e.g., a metric such as height, distance, pressure, acceleration). For example, a foot contact event may be required to have a threshold amount of force or a threshold amount of acceleration in a particular direction. Accordingly, for a foot contact event to match the template, the event may be required to exhibit the threshold acceleration along the x-axis in one example or the threshold amount of force in another example. Other types of event values may also be used as needed or desired. Event duration, on the other hand, may include duration requirements that define a maximum or minimum amount of time allowed or required for a particular event. Accordingly, an event may be required to have a minimum duration or be below a maximum duration to qualify as an event match with the template.

One example of an action template may include specified event types, such as one or more from among examples including: the last time the template successfully matched a set of events; left foot launch; left foot strike; right foot launch; right foot strike; local maxima in the vertical acceleration measurements of the left foot; and/or local maxima in the vertical acceleration measurements of the right foot. The action template may further include specified constraints, such as one or more from among examples including: there should be a left foot launch; there should be a right foot launch; there should be a left foot strike; there should be a right foot strike; left and right foot launches should occur before the left and right foot strikes; there should be no additional left or right foot launches or strikes, and the like, etc. The above event types and constraints may be combined in various manners to define an action template corresponding to a two foot jump, a single foot jump and/or other user actions. Accordingly, in an example, not only might the set of events be required to match the specified event types of the template states, but they may also be required to meet the defined constraints.

If the set of events does meet a specified number (e.g., 25%, 50%, 75%, 90%, 100%) of the template constraints, the system may record the set of events as a possible template match in step 1130. After recording the possible template match or upon determining that the set of events does not meet the specified number of template constraints, the system may determine, in step 1135, whether there are more sets of events (from the identified sets of events) to analyze. If so, the system may return to step 1120 to pick an un-analyzed set of events to process. If, however, no other sets of events need to be analyzed, the system may proceed to step 1140, where the system determines whether possible template matches were found. For example, the system may determine whether template matches were recorded in step 1130. If not, the system may proceed to step 1160 to determine whether more events are expected for processing.

If, on the other hand, possible template matches are found (e.g., match identified and recorded), the system may select a best match in step 1145. Selecting a best match may be performed in various manners including those described herein. Once the best match is selected, the system may process the matching events in step 1150 to determine one or more additional details of the user's action. For example, the matching events may be processed for jump height, speed, pace and the like and/or combinations thereof. In step 1155, the system may present the matching template (e.g., display that the user has performed an action corresponding to the template) and/or the additional details. The system may then determine whether additional events are expected for processing in step 1160.

In one or more arrangements, the set of events may be analyzed incrementally, event by event. When an event is identified, constraints related to the template state that that event is being considered for matching purposes are analyzed. If the constraints are not satisfied, the incremental search is back-tracked (to varying degrees depending on which constraints are not satisfied) and new events are identified. For example, failure to meet/match optional constraints might not cause the system to back-track the search. When the incremental search has found an entire set of events that meet all the template constraints, the match is scored and recorded. According to one or more embodiments, the best match (by score) is stored so that when there are no additional events to analyze, the best match information is already selected.

Combinations of events may be explored according to a tree structure defined by the relative temporal occurrence scoring parameters of each state in the template. Accordingly, when a particular event occurrence indicates that no subsequent template states can be matched, or that the no other event occurrences for a particular state will match, the search may be stopped at that point in the tree. Moreover, a new set of event occurrences may then be explored. This approach may enable the template matching process to more quickly and more efficiently discard non-matching events or a non-matching set of events.

Figure 12:
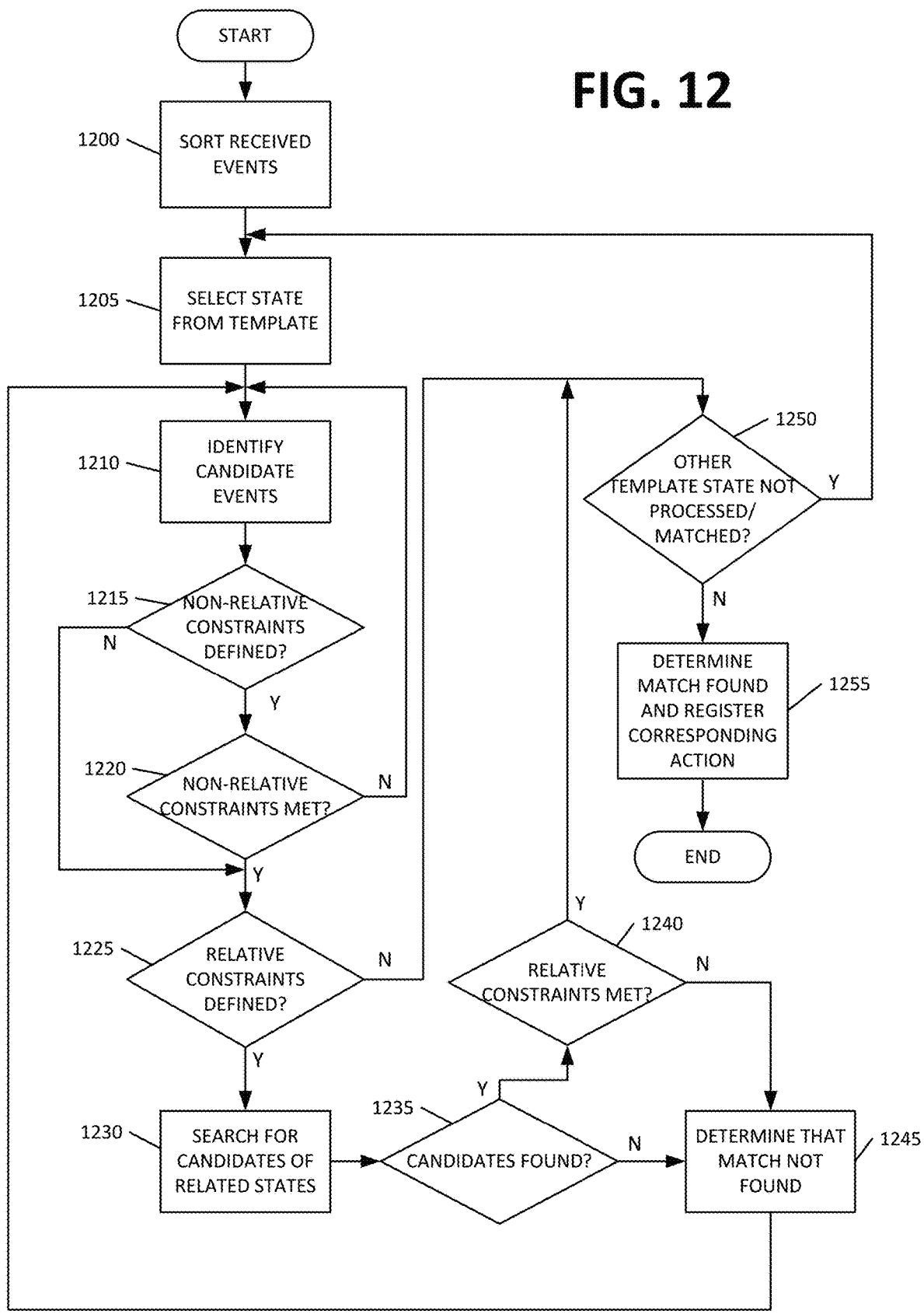
FIG. 12 illustrates another example template matching process.

FIG. 12 illustrates another example template matching process that may be repeated for each of one or more templates (e.g., step 1005 of FIG. 10). For example, upon receiving one or more events (e.g., a stream, group, set, etc.), an activity processing system may sort the events in step 1200. As an example, the events may be temporally sorted.

In another example, the events may be stored based on an order in which the events were detected as described with respect to step 1020 of FIG. 10. Once sorted, the system may, in step 1205, select a state defined in the template to initially search for in the sorted events. The template state may be variously selected, such as based on one or more factors and considerations. As examples, the template state may correspond to (i) the first or initial event of a particular action represented by a template or (ii) the ending event of that action. In other examples, the template state may correspond to a highest priority state within the template. In yet other examples, the template state may correspond to any of the states in the template.

In step 1210, the activity processing system may identify candidate events matching the event type of the selected template state. In one example, events may be sorted (as described in step 1200) by storing or organizing the events according to categories of event types. In some arrangements, generated events might not be sorted and instead, may be stored randomly upon generation and/or receipt. Additionally or alternatively, events may be stored in a variety of manners: e.g., completely at random, by event type, by event type and temporal order of occurrence, by event type and particular measurement value, etc. Accordingly, in one example, the processing system may identify candidate events by retrieving events from the category corresponding to the selected template state. Various event type matching algorithms and methods may be used as described herein. In some embodiments, the type of sorting of the events may provide efficiencies to the matching algorithms. For example, a sequential matching algorithm may benefit from temporally sorted events.

Once candidate events have been identified based on event type, the activity processing system may evaluate each of those candidate events to determine whether the candidate event matches the constraints of the template state specified in the template. For example, the constraints of the template state may correspond to the constraints described with respect to FIG. 11. Accordingly, in step 1215, the activity processing system may determine whether non-relative constraints are defined for the template state. If so, the system may proceed to step 1220, to determine whether a candidate event meets non-relative constraints of the template state (e.g., constraints that are not dependent on other template states). For example, a value of a candidate event may be compared to a value constraint/requirement of the template state. In another example, the duration of the candidate event may be compared to a duration constraint of the template state. If none of the candidate events meet the constraints of the template state, the activity processing system may return to step 1210 to search for other candidate events matching the event type of the selected template state.

If, however, one or more candidate events meet the non-relative constraints or if the template state does not include non-relative constraints, the activity processing system may determine, in step 1225, whether relative constraints are defined for the template state. Relative constraints may include constraints dependent on other template states or available information like aggregate statistics measured from prior occurrences of a particular event type. For example, a relative constraint may include a temporal relationship with another template state. If relative constraints are defined, in step 1225, the activity processing system may, for each of the one or more other template states corresponding to the relative constraints, search for one or more candidate events matching the event type of the other template state. If one or more candidate events are identified in step 1230 (based on event type), the activity processing system may determine, in step 1240, whether those candidate events meets the relative constraints of the selected template state. For example, if the template requires a first template state to be within 80 milliseconds of a second template state, the activity processing system may evaluate whether each of the candidate events for the second template state meets the 80 millisecond requirement of the first template state.

If the candidate events for the related template state do not match the relative constraints or if no candidate events are found, the activity processing system may determine that a match was not found in step 1245. In such a case, the activity processing system may return to step 1210 to identify and evaluate other candidate events that may match the template state. If, however, one or more candidate events of the related template state do meet the relative constraints of the selected template state, the activity processing system may determine, in step 1250, whether other (e.g., remaining) template states have not been processed or matched. If that determination is negative, the activity processing system may determine in step 1255 that the template has been matched and register the action as having been performed by the user. Additionally or alternatively, additional activity information may be generated based on the matching events. If, on the other hand, in step 1250, the determination is that one or more template states in the template have not yet been matched, the activity processing system may return to step 1205 to select one of the remaining unmatched template events, i.e., for processing starting with step 1210.

In one or more arrangements, upon determining that at least one state in a template has not been matched (e.g., in decision steps 1220 and/or 1240), the activity processing system may end evaluation of that particular template. In such examples, upon ending evaluation, an activity processing system may select a new template to evaluate (e.g., if any new template awaits relative to the START step of FIG. 12). In other examples, the activity processing system may continue evaluating that particular template as to the at least one template state, i.e., toward finding a match. Such continued evaluation may be variously configured, e.g., to continue for a specified amount of time, for a specified number of events, until some another (e.g., higher priority) process interrupts such processing, until certain power has been consumed or remains (e.g., in battery powered systems), or until other condition(s) are satisfied, or combination(s) of any of the above or other condition(s) are satisfied. Upon completing evaluation of the particular template in accordance with the configuration, the activity processing system may then select a new template. The configuration for continued evaluation may be specific to the particular template, specific to various templates (i.e., not applicable to other individual or group(s) of template(s)), generic among all templates, or specific to one or more activity types. Accordingly, where any such configuration applies to the particular template, or if the particular template does not provide for continued evaluation once at least one of the template's states is determined not to be matched, the activity processing system might end evaluation of the particular template. In alternative examples, the activity processing system might continually (and, subject to physical and practical limitations, indefinitely) evaluate a particular template.

When an activity processing system ends evaluation of a first template and transitions to evaluation of a second template, the activity processing system may require a specified amount of time. This time may result in perceived lag to the user. Accordingly, in some arrangements, the activity processing system may provide the user with notification that the activity processing system is transitioning to consideration of another template. Additionally or alternatively, the activity processing system may provide the user with various information, images, feedback, etc. to occupy the user's attention while the transition is completed. For example, the activity processing system may display statistics relating to a previously evaluated template, current activity metrics, information about a location in which the user is performing activity and the like and/or combinations thereof.

The activity processing system may also perform calibration or re-calibration of one or more sensors, of a template and/or of the template matching process. For example, if the activity processing system determines that a template has not matched in a previous number of attempts (e.g., 10, 20, 50, 100, etc.), the activity processing system may automatically trigger a re-calibration process. Alternatively, the calibration or re-calibration process may be triggered by user input. For example, a user may determine that the activity processing system should have detected a two foot jump, but did not. Accordingly, the user may provide input (e.g., a button press, touch input, etc.) to trigger calibration or re-calibration. In one example, calibration or re-calibration may include increasing sensitivity of one or more sensors to a level where an event or action that should have been detected is detected. In another example, calibration or re-calibration may include modifying constraint parameters (e.g., scoring distribution parameters as described herein) such that a candidate event that did not score as a match, scores as a match with the constraint. In yet another example, re-calibration may include modifying a match tolerance so that a candidate event that did not match, would match. Alternatively or additionally, calibration or re-calibration may include modifying sensor parameters, template parameters and/or template matching parameters to exclude events or actions that should not have been detected. For example, sensor sensitivity may be decreased, template constraints or states may be narrowed and/or template matching thresholds may be decreased. Calibration or re-calibration may further be performed based on other factors or parameters including user characteristics, environmental characteristics, social characteristics and the like. For example, a user's shoe size may be used to calibrate sensor sensitivity or scoring distribution parameters in a template. In another example, weather conditions of a user's performance may affect sensor sensitivity or a threshold with which matches are evaluated. Various other modifications to parameters of the sensing, detecting and matching process may be incorporated to calibrate or re-calibrate event and action detection.

In one or more examples, an activity processing system may search for candidate events (e.g., in step 1230) that match the event type of the related template state and that match the relative constraints of the selected template state. Accordingly, if the template requires that the template state occur within 500 milliseconds of another template state such as a foot launch state, the activity processing system may search for candidate foot launch events that are within 500 milliseconds of a detection time of the template state to insure that the relative constraint is met. In one or more arrangements, the activity processing system may search for candidate events for a predefined amount of time. For example, the searching period may be defined by a relative time constraint between the template state and the related template state. In a particular example, if the template state includes a constraint that a related template state must occur within 5 seconds, the searching period may be defined as 5 seconds after detection of the template state. If candidate events are found (e.g., per step 1235), the activity processing system may return to step 1215 to determine whether the candidate event(s) of the related template state meet the constraints applicable to that related template state. Accordingly, the activity processing system may perform a recursive process whereby the activity processing system determines whether the related template event exists.

The activity processing system may further be configured to non-dimensionalize, normalize or scale events. Non-dimensionalization or scaling of events may correspond to scaling or non-dimensionalizing time, an event value, an event duration and the like. In one example, an absolute time at which events were detected is converted to a relative time. For example, a temporal location of the events may be defined relative to an overall amount of time between the first and second predefined events. In a particular example, the time at which an event occurs may be defined as or scaled to a percentage of the duration between the predefined events. Thus, the identified first predefined event (e.g., an action starting event) may be set as time 0 while the second identified event (e.g., an action ending event) may be set as time 100 regardless of the actual time span between the two events. The events existing between the first and second predefined events may thus be scaled to a time between 0 and 100. The non-dimensionalization of a template and corresponding event window allows a system to detect actions for varying speeds of performance. Thus, regardless of whether the action is performed over a span of 10 seconds or 2 seconds, the system may detect the corresponding combination of events as matching the action template. In some examples, non-dimensionalization may be performed regardless of an amount of time between two or more events. In other examples, non-dimensionalization might only be performed if the amount of time between the two or more events are below a specified threshold, within a window of durations, above a specified threshold and the like and/or combinations thereof.

In another example, non-dimensionalization or scaling may include normalization of event values such that they are more readily comparable. For example, a sensitivity of a force sensor in a right shoe may be greater than the sensitivity of a force sensor in a left shoe. Accordingly, the force values of the right shoe sensor and the left shoe sensor may be normalized to facilitate comparison and processing of the values. In a particular example, if a constraint includes a force detected by a right shoe being within 10% of a force detected by a left shoe, normalization may be needed to insure appropriate matching of events and constraints, e.g., when sensitivity differences exist.

According to other aspects, templates may further include predefined exclusion events. Exclusion events may be used to define conditions under which one or more candidate events are disqualified from matching the template. The exclusion events may be defined on an action-by-action (e.g., template-by-template) basis or may be defined to apply to all actions/templates. In the example of a jump template, an exclusion event may correspond to a foot contact event existing between a foot launch event and another foot contact event since a jump generally does not include an intermediate foot contact event. If an exclusion event is detected, the series of events may be removed from consideration as a match with the template.

Additionally or alternatively, determining whether a specified template or event thereof has been matched may further include a level of tolerance. For example, if the one or more events matches 90% of the specified template, the events may be considered a match and the corresponding action may be registered. In a particular example, the template may include 15 events while the series of events matches 14 of those 15 events. In such a case, with a 90% tolerance level, the system may determine that the series of events matches the template. Other factors beyond matching the type of events in the templates may be used. For example, timing of the events may also be compared to determine whether a match exists. As with matching the type of events detected, a tolerance level may be defined to allow for deviations in timing of the events.

Template matching processes may be invoked at various times and under various conditions. For example, template matching may be performed periodically, in response to a trigger by an event aggregation and storage unit, and/or based on user input into the system. In a particular example, an event aggregation and storage unit may trigger the template matching process upon determining that a threshold amount of events has been received from one or more sensor systems and stored. In another example, a user may select an option or function to process activity data from a recent activity session. In one or more configurations, the type and amount of event information that is processed during template matching might also be limited or specified based on one or more factors. For example, the template matching process may use all event occurrences since a last positive match of the activity template. In another example, the template matching process might only use event occurrences within a pre-specified temporal window. In still another example, the template matching process may use only event occurrences that have met prior filtering criteria (such as meeting certain intra- or inter-event quality checks). Accordingly, various methods, parameters and specifications may be used to enhance efficiency and processing speed.

Figure 13A:
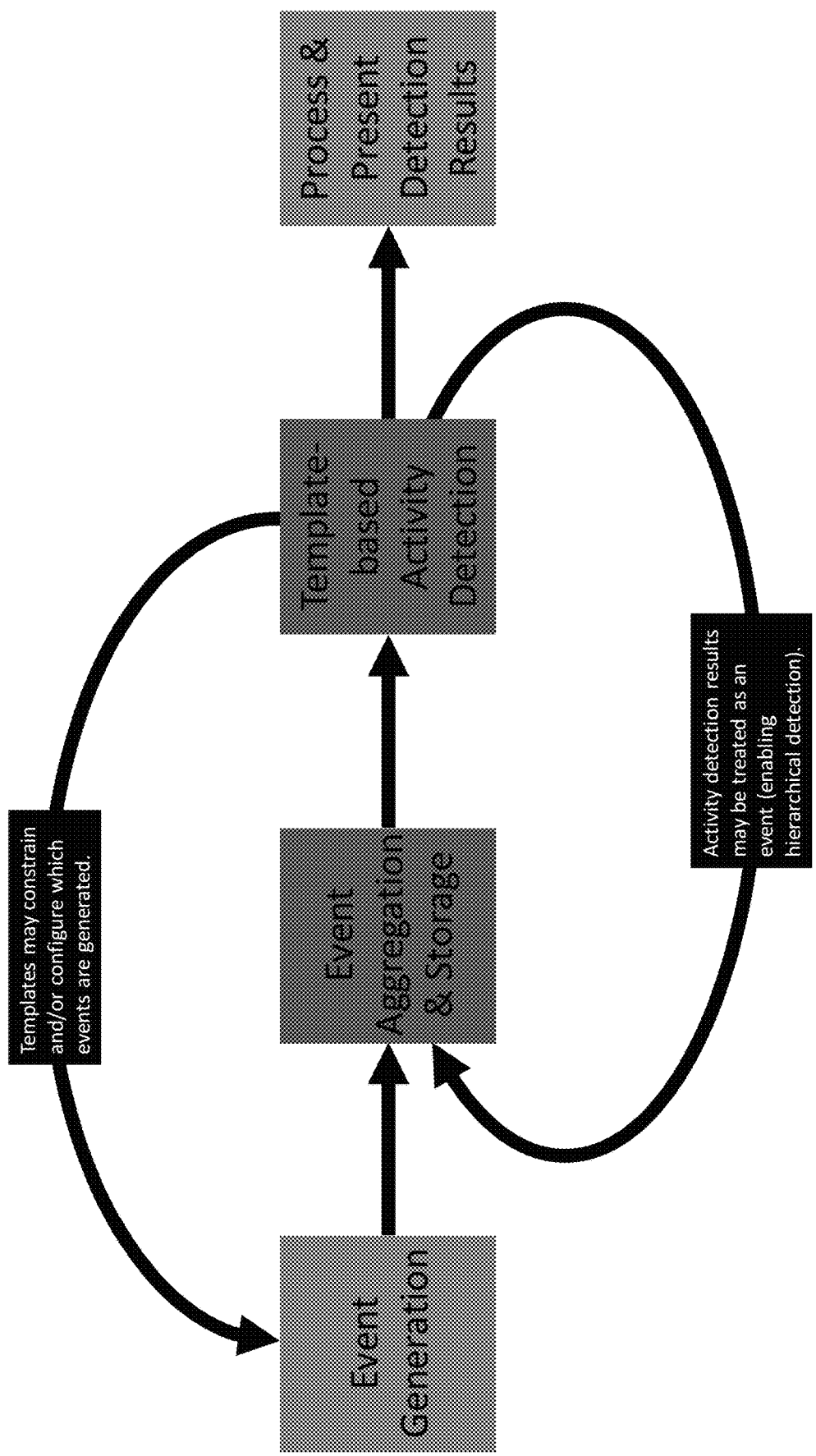
FIGS. 13A-13D illustrate example data processing flows for template matching.

FIGS. 13A-13D illustrate example data processing flows for identifying actions performed by the user using various types of devices, sensors and the like. For example, FIG. 13A illustrates various processes that may be performed by one or more devices. The processes may include event generation, event aggregation and storage, template-based activity detection and processing/presentation of detection results (e.g., determining metrics associated with the detected activity and presenting such metrics to the user). These processes may be performed by a single device or multiple devices. In one example, all of the described processes may be performed by an activity processing device, a sensor system, a computing device, a mobile communication device, a cloud system, a server and the like. In another example, performance of the various processes may be divided amongst a plurality of the aforementioned devices. Accordingly, in an example, event generation may be performed by a sensor system while event aggregation and storage, template-based activity detection and processing and presentation of detection results may be performed by another device such as the activity processing system. In yet another example, the sensor system may be configured to provide event generation, the activity processing system may be configured to provide event aggregation and storage as well as template-based activity detection and a third device (e.g., a mobile communication device or computing device) may be configured to process and present detection results.

Figure 13B:
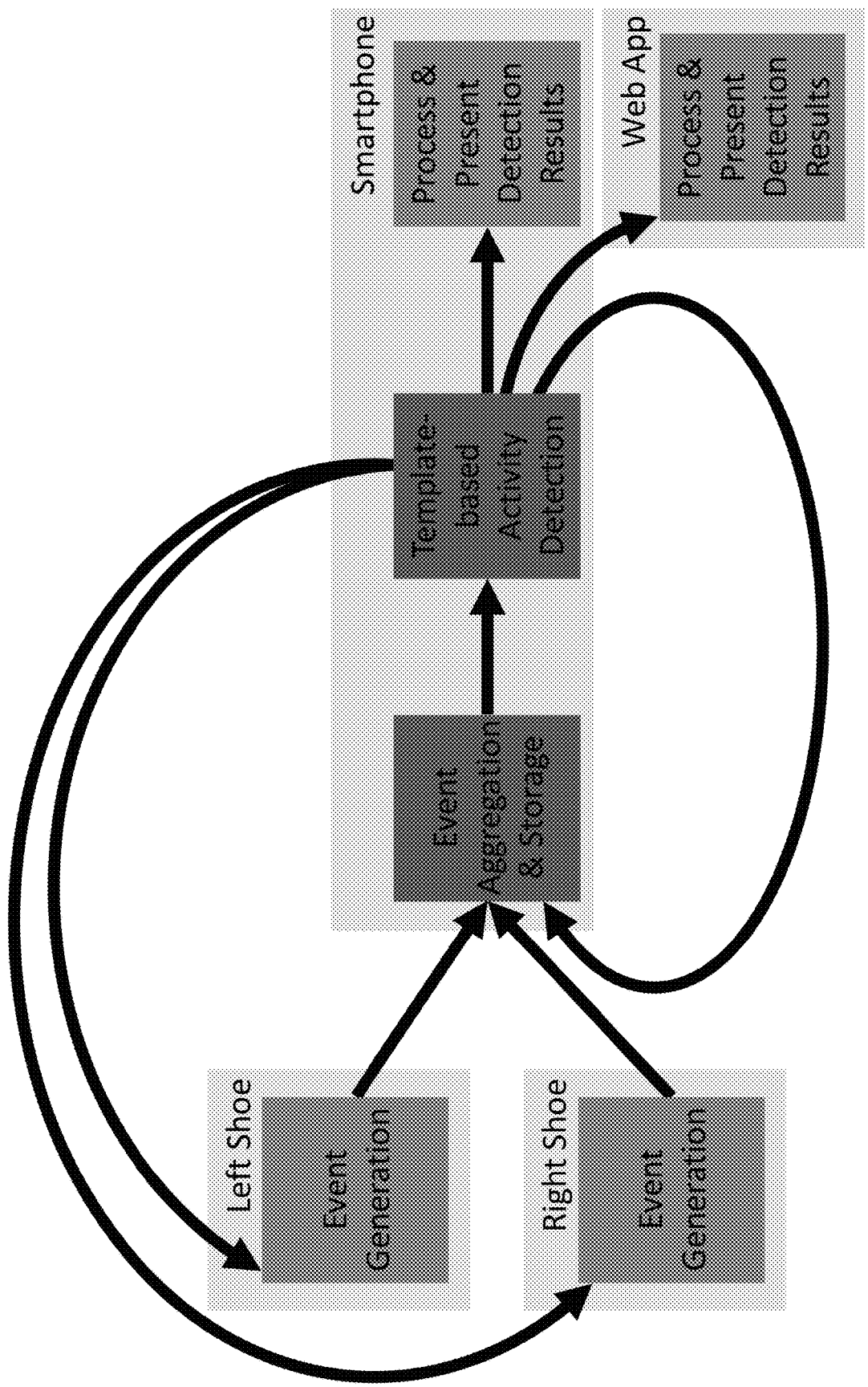

FIG. 13B illustrates an example configuration in which 4 devices or systems are used to perform activity detection processes. For example, a user may wear two shoes, a right shoe and a left shoe, each with its own sensor or sensor system. Each of those sensors or sensor systems may be configured to generate events based on detected sensor signals. A smartphone (or other mobile communication device) may be configured to receive the generated event information, aggregate and store the event information and perform template-based activity detection based on the event information. The results of the template-based activity detection may be processed to generate metrics and other types of activity information for the detected action by the smartphone or by another device such as a web application, system or server. Accordingly, a user may be able to view detected activity information through multiple devices.

Figure 13C:
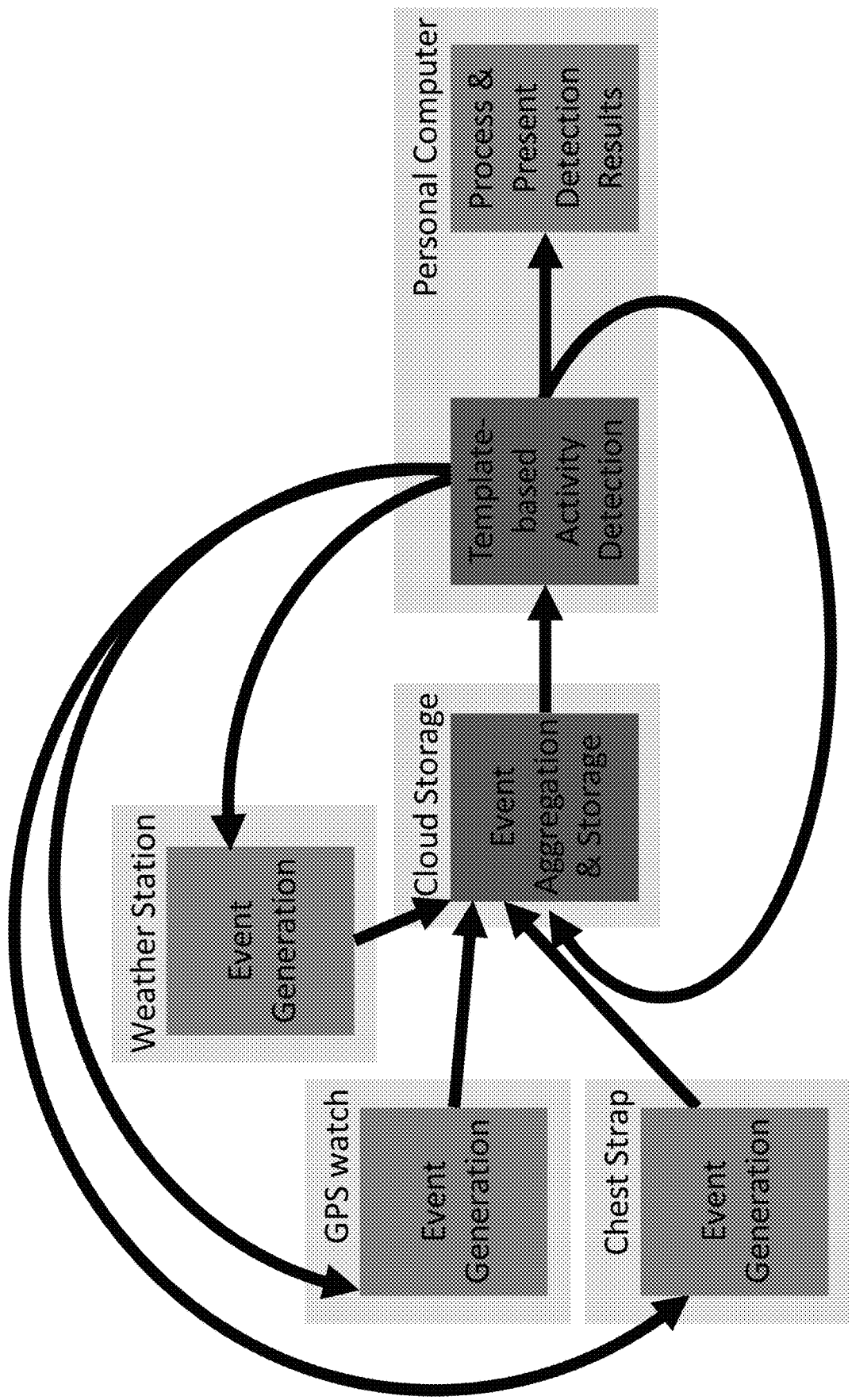

FIG. 13C illustrates another example system configuration whereby events may be generated by various types of devices including a chest strap (e.g., to detect heart rate and/or body temperature), a location determination device such as a GPS watch and an environmental detection system such as a weather station. The event information generated by these devices may be collected and stored in a cloud device, system or server for accessibility through a public or private network. The aggregated event information may then be retrieved by one or more other devices such as a personal computer, smartphone, other mobile communication device, tablet computer, game consoles, web servers and the like. Upon retrieval, the personal computer may perform template-based matching and activity detection and process and present detection results.

Figure 13D:
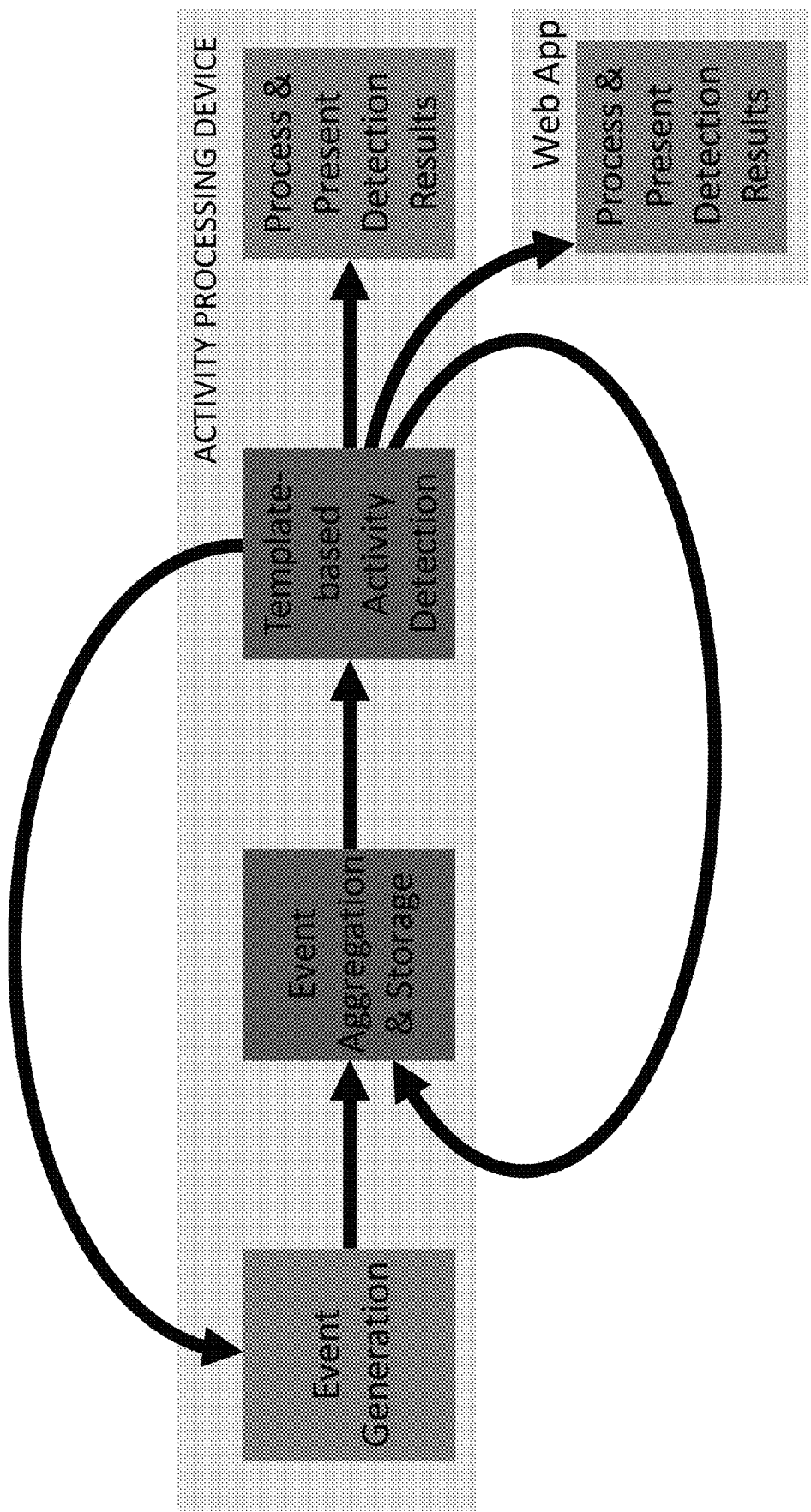

FIG. 13D illustrates an example system in which all of the above-described processes may be performed by a single device, e.g., an activity processing device or system. For example, events may be generated by the activity processing system based signals from sensors included therein, user input, activity processing system output (e.g., alerts, displays, notifications, sounds, conditions, etc.) and the like and/or combinations thereof. The activity processing system may then process the events to perform template-based activity detection. Detection results may be shared with other devices as desired or needed. Accordingly, activity detection results may also be processed and presented by a web server, a cloud system, a mobile computing or communication device, game consoles, personal computing devices and the like.

FIG. 14 illustrates an example template. The example template 1400 may be defined in the form of an array. The first element in a template state array (e.g., template state arrays 1401*a*-1401*h*) is the index number of the state in the template (starting with zero). The second element in each of the template state arrays is the text label for a specific event type. For excluded template states (e.g., represented by arrays 1401*e*-1401*h*), the third and fourth elements in the template state array are prior template state indices. In one configuration, the interpretation of the excluded template state syntax is: every known occurrence of the excluded event type (specified by the second element in the template state array) should not occur between the matching occurrences of the prior template state events specified by the last two array elements.

For included template states, template state array elements 3 through 9 specify how to score the relative event occurrence time stamp of a matching or candidate event. For example, elements 3 through 9 may represent various constraints that must be matched. If the value of array element 3 is −1, the temporal reference point is the time that the template match process was initiated. Otherwise, the value of array element 3 is a reference to another template state, and the temporal reference point is the event occurrence time stamp of the matching event for the prior template state. Array element 4 is the temporal offset applied to the temporal reference point. The temporal offset, in one or more example embodiments, as appropriate to activities and/or events, may be in units of milliseconds.

Array element 5 describes the type of scoring distribution applied to the relative time value. Examples distributions include: ESP_DIST_INCREASING, ESP_DIST_DECREASING, and ESP_DIST_ABSVAL_DECREASING. In one or more example embodiments, these three distributions are the permissible types. Array elements 6 through 9 are the parameters of the distribution. In one example process of scoring the relative occurrence time of an event, assume the following: T_e is the event occurrence time of the (potentially matching) event, T_o is the temporal reference point, dT is the millisecond offset, and P_1, P_2, P_3, and P_4 are the distribution parameters. Note, in some examples, the following rules may be enforced: P_1<= P_2<=P_3<=P_4; and, additionally, 0<=P_1 if the distribution is ESP_DIST_ABSVAL_DECREASING. The relative event occurrence time may then be scored according to the following example formulas:

If the scoring distribution is type ESP_DIST_INCREASING, then the score, S, may be computed as:

$$S=0 \text{ if } (T\_e-T\_o-dT)<P\_1 \ (T\_e-T\_o-dT-P\_1)/ \\ (P\_2-P\_1) \text{ if } P\_1<=(T\_e-T\_o-dT)<P\_2 \\ 1+(T\_e-T\_o-dT-P\_2)/(P\_3-P\_2) \text{ if } P\_2<= \\ (T\_e-T\_o-dT)<P\_3 \ 2+(T\_e-T\_o-dT-P\_3)/ \\ (P\_4-P\_3) \text{ if } P\_3<=(T\_e-T\_o-dT)<P\_4 \ 3 \text{ if } \\ P\_4<=(T\_e-T\_o-dT)$$

If the scoring distribution is type ESP_DIST_DECREASING, then the score, S, may be computed as:

$$S=3 \text{ if } (T\_e-T\_o-dT)<P\_1 \ 3-(T\_e-T\_o-dT-P\_1)/ \\ (P\_2-P\_1) \text{ if } P\_1<=(T\_e-T\_o-dT)<P\_2 \\ 2-(T\_e-T\_o-dT-P\_2)/(P\_3-P\_2) \text{ if } P\_2<= \\ (T\_e-T\_o-dT)<P\_3 \ 1-(T\_e-T\_o-dT-P\_3)/ \\ (P\_4-P\_3) \text{ if } P\_3<=(T\_e-T\_o-dT)<P\_4 \ 0 \text{ if } \\ P\_4<=(T\_e-T\_o-dT)$$

If the scoring distribution is type ESP_DIST_ABSVAL_DECREASING, then the score, S, may be computed as:

$$S=3 \text{ if } |T\_e-T\_o-dT|<P\_1 \ 3-(|T\_e-T\_o-dT|-P\_1)/ \\ (P\_2-P\_1) \text{ if } P\_1<=|T\_e-T\_o-dT|<P\_2 \\ 2-|T\_e-T\_o-dT|-P\_2)/(P\_3-P\_2) \text{ if } \\ P\_2<=|T\_e-T\_o-dT|<P\_3 \ 1-|T\_e-T\_o-dT|- \\ P\_3)/(P\_4-P\_3) \text{ if } P\_3<=|T\_e-T\_o-dT|<P\_4 \ 0 \\ \text{ if } P\_4<=|T\_e-T\_o-dT|$$

Using the above equations, for a match to be found, the relative temporal occurrence score must be greater than 0.

Template state array elements 10 through 15 specify how to score the event generation time stamp. Array element 10 is a flag indicating whether or not the event generation time stamp should be scored. If the value is 0, no score is computed. If the value is not 0, the event generation time stamp is scored. Array elements 11 through 15 are analogous to elements 5 through 9; and may use an analogous score computation. In one arrangement, there might be no reference value applied to the event generation time stamp; just an offset. If the event generation time stamp is scored, a matching event to the template state must achieve a score above zero.

Analogous to the event generation time stamp scoring, array elements 16 through 21 specify if and how the event value should be scored. If the event value is scored, a matching event to the template state must achieve a score above zero.

Finally, template state elements 22 through 27 specify if and how the event duration should be scored. The event duration may be either (i) the time difference between the event occurrence time stamp of the event being scored and the event occurrence time stamp of the immediately subsequent (in time) occurrence of the same type of event; or (ii) if the event occurrence being scored is the most recent occurrence of that particular event type, the event duration is the time difference between the event occurrence time stamp and the time that the template match process was initiated. If array element 22 is set to 0, no score is computed. If it is set to −2, the event duration is relativized by the time difference between the event being scored and time that the template matching process was initiated before being scored. Otherwise, the event duration may be scored analogously to the event generation time stamp and the event value. As above, if the event duration is scored, a matching event to the template state must achieve a score above zero.

As noted herein, other types of constraints (e.g., beyond duration, event generation time stamp, and relative event occurrence time stamp) may be defined. Accordingly, further values and/or parameters may be added to the template state array. For example, the template state array may be expanded to include further array parameters and value. In other examples, the template state array may be reduced in size if one or more of the above-described constraints are not needed or desired.

In some examples, temporal constraints may be defined based on an earliest time that an event time stamp could have occurred. Based on that threshold, the algorithm may better (e.g., more efficiently) determine when a set or group of events, stored by type and chronology, can no longer provide a possible match. Moreover, relative temporal constraints may reference earlier template states. Accordingly, when the algorithm determines that no candidate events is able to satisfy the relative temporal constraint, a processing system may determine that the system may need to consider a different event for at least one of the referenced template. Thus, the incremental search can be backtracked up to the referenced template states. Additionally or alternatively, template states that are not referenced by subsequent reference states (i.e., are leaves in the tree defined by constraint references) may be searched at any point (e.g., as opposed to incrementally). Exclusion constraints, similar to relative temporal constraints, may reference earlier template states. As such, a failed exclusion constraint may enable the incremental search to be backtracked up to the referenced template states.

Figure 15:
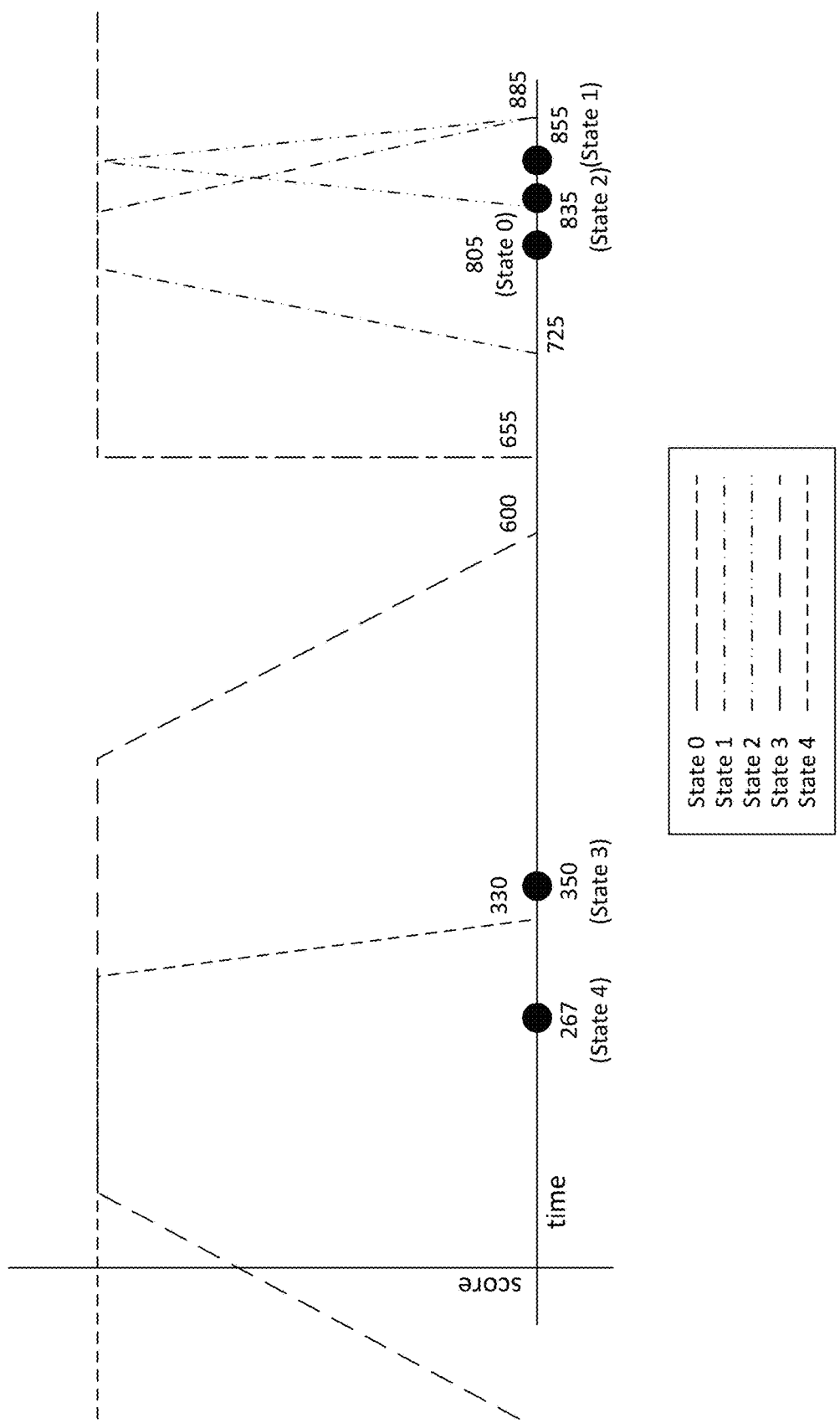
FIG. 15 illustrates an example action template matching graph.

FIG. 15 illustrates an example event graph in which various events are identified as matching a template based on scoring of the relative event occurrence time stamp of candidate events. Each of the different patterned lines represents the scoring distribution for a different candidate or matching event, where each of those different events match one of the following states (each state is defined on its own line) in a template:

0: −1,−200,"ESP_DIST_INCREASING",0,0,0,0
1: 0,0,"ESP_DIST_ABSVAL_DECREASING",20,40,60, 80
2: 1,0,"ESP_DIST_ABSVAL_DECREASING",0,10,20,30
3: 0,−500,"ESP_DIST_ABSVAL_DECREASING",150, 200,250,300
4: 3,0,"ESP_DIST_DECREASING",−50,−40,−30,−20

By way of example, the elements in state 1 may be interpreted as follows:

1—State identifier

0—Indication that state 0 is the temporal reference point

0—Indication that relative to the timestamp of the event that matches state 0, not applying any offset (in milliseconds)

"ESP_DIST_ABSVAL_DECREASING"—Indication of the kind of cost/scoring distribution curve 20—to score a 3, the timestamp of the event that matches state 1 needs to be within 20 milliseconds of the timestamp of the event that matches state 0

40—to score between 2 and 3, the timestamp of the event that matches state 1 needs to be at least 20 milliseconds, but no more than 40 milliseconds, different from the timestamp of the event that matches state 0

60—to score between 1 and 2, the timestamp of the event that matches state 1 needs to be at least 40 milliseconds, but no more than 60 milliseconds, different from the timestamp of the event that matches state 0

80—to score between 0 and 1, the timestamp of the event that matches state 1 needs to be at least 60 milliseconds, but no more than 80 milliseconds, different from the timestamp of the event that matches state 0

Accordingly, if the temporal offset were modified to −200 milliseconds, for example, then the temporal constraint on an event to match state 1 would be that a candidate event must occur +/−80 milliseconds from 200 milliseconds before the time stamp of the event that matches on state 0. So, if the matching event for state 0 occurred at time 1290, the temporal constraint for state 1 would translate to: after 1010 (1290−200−80) and before 1170 (1290−200+80). In the graph, the time span of each of the state scoring distributions corresponds to a range of times during which a matching event may exist.

Figure 16:
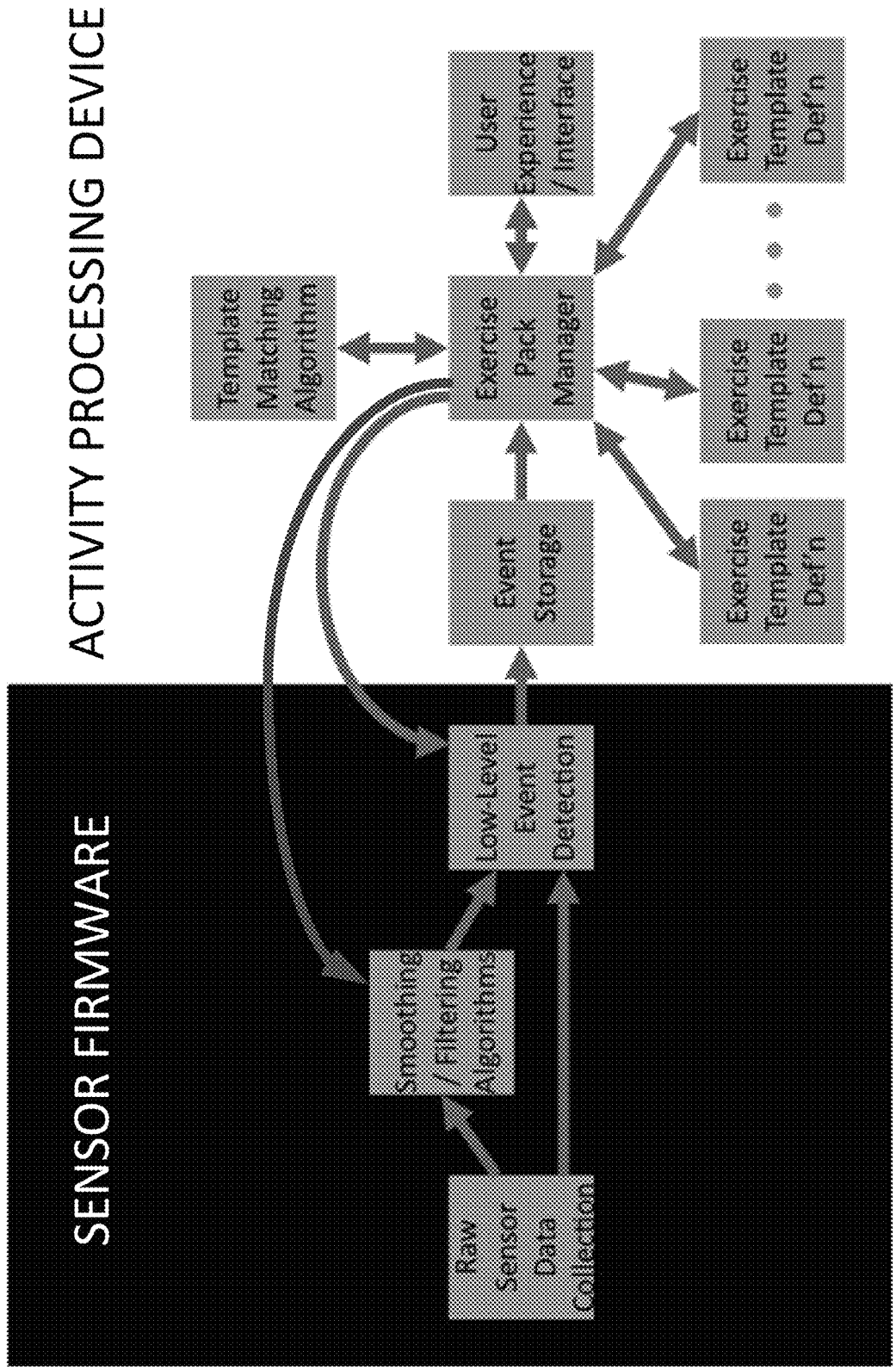
FIG. 16 is an example diagram of a data flow between a sensor system and an activity processing system.

FIG. 16 illustrates an example data and processing flow that may be used to analyze sensor data and events and detect various actions performed by a user during an activity. For example, a sensor or sensor system having sensor firmware may be configured to collect raw sensor data, smooth and filter the data, as needed, and to provide granular or low-level event detection as described herein. The sensor or sensor system may be configured with various circuits, processors and combinations of software and/or firmware to provide the requisite processing. Once low-level events have been detected, the low-level event information may be passed to an activity processing device or system. The activity processing device or system may be integrally housed or may be physically separate from the sensor or sensor system. In one example, an activity processing device or system may communicate with the sensor system via wireless or wired communications including short range wireless protocols such as BLUETOOTH and BLUETOOTH—LOW ENERGY, cellular communications, Wi-Fi, satellite communications and the like. The activity processing system may store the events in a cache, buffer or other memory systems and subsequently process events against predefined action templates. In one or more examples, the activity processing device or system processes events incrementally and/or as a window of events. Based on comparisons between the processed events and the action templates, the system may identify one or more actions that were performed, e.g., during the window of events.

Figure 18:
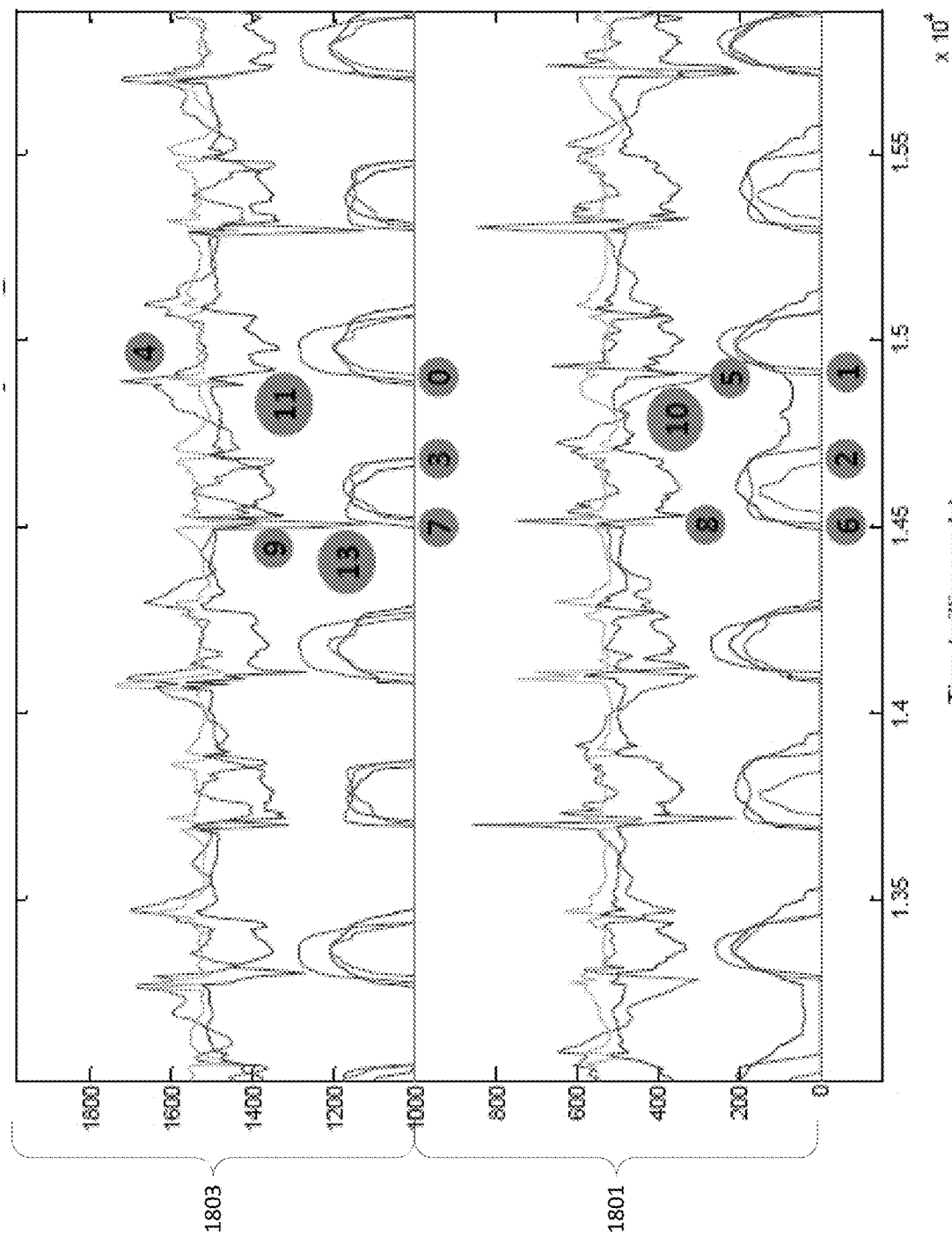
FIGS. 18-20 illustrate example signal streams and events identified therein.
Figure 19:
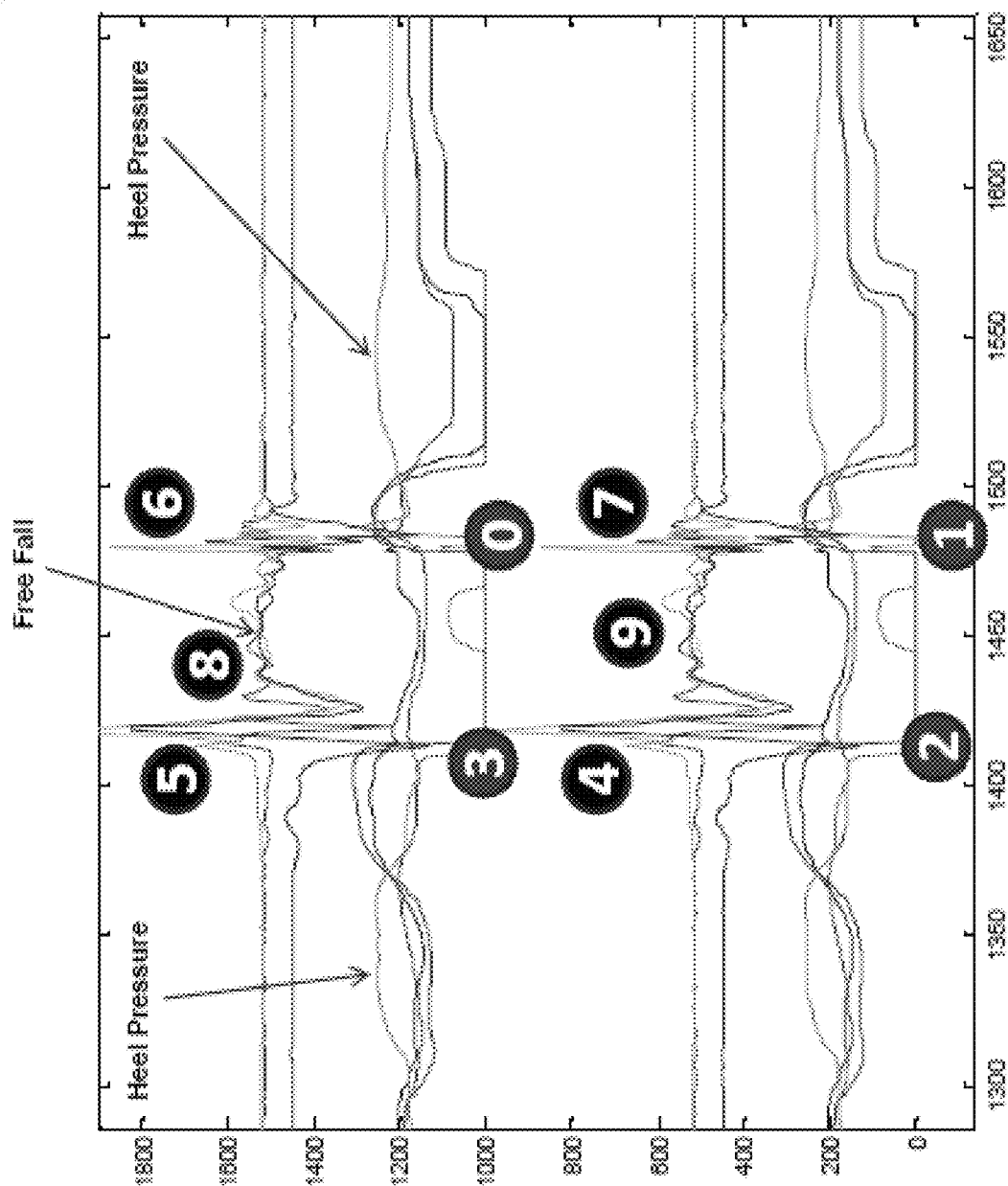
Figure 20:
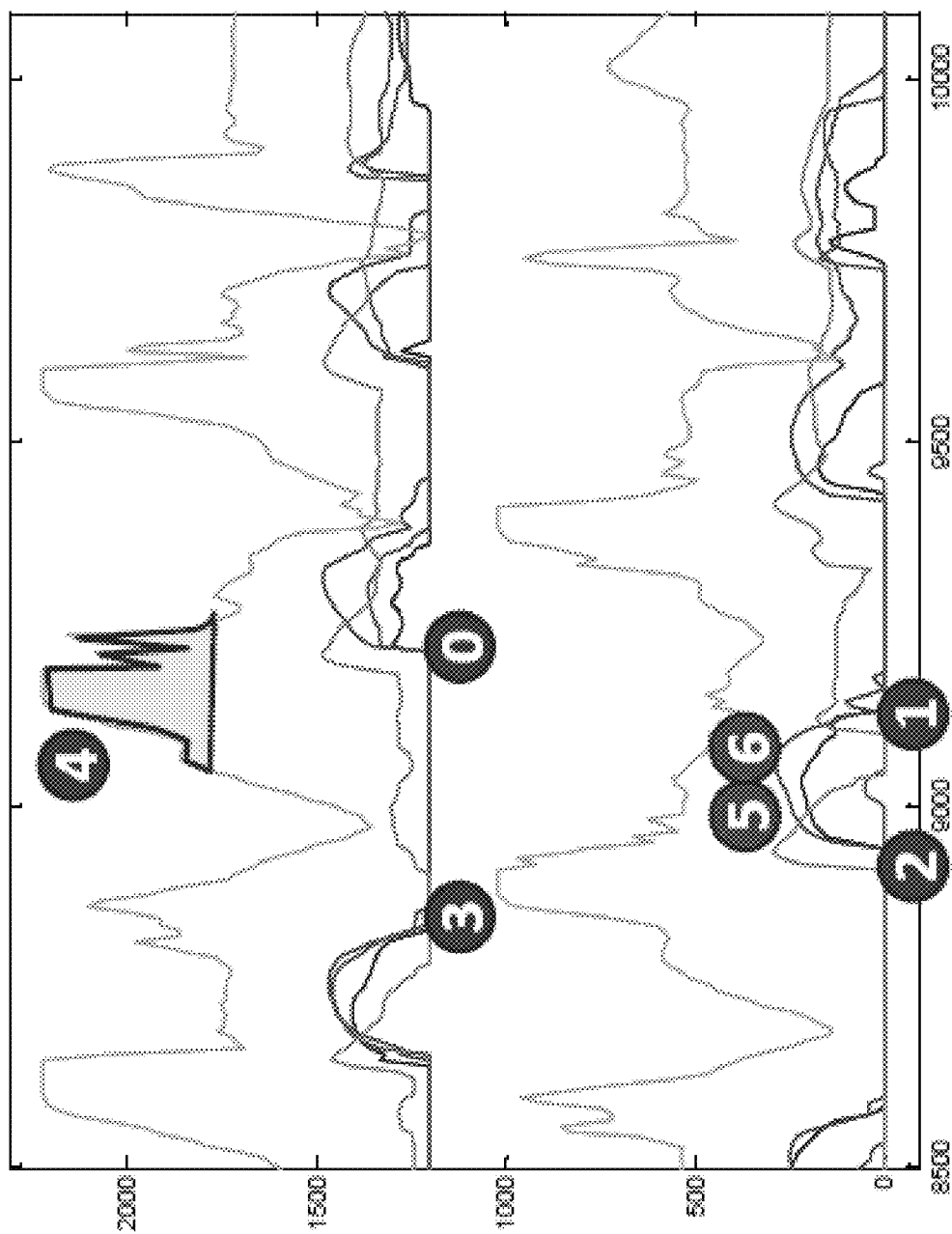

FIGS. 18-20 illustrate example event identification within signal streams for shoe based sensors. For example, FIG. 18 illustrates example signals from two shoe-based sensors during user performance of a jumping jack exercise or drill. The upper signal 1803 represents the signal from a right shoe-based sensor and the lower signal 1801 represents the signal from a left shoe-based sensor. Labels 0-13 may represent various detected events within the signal stream. For example, the labels may represent the following detected events or states:

0) Jump right strike
1) Jump left strike
2) Jump left launch
3) Jump rith launch
4) Integral of right x acc above threshold
5) Integral of left X acc below threshold
6) Jump left strike
7) Jump right strike
8 and 10) Minimum derivative left z acc
9 and 11) Minimum derivative right Z acc
12) Integral of left X acc above threshold
13) Integral of right X acc below threshold The set of events identified by labels 0-13 may correspond to a jumping jack action template. Accordingly, when a set of events matching events 0-13 are detected in a specified order and/or timing, the system may determine that the user has completed one jumping jack. In another example, a jumping jack template may specify that 7 events must be detected in a particular sequence and within a given timing. These events may include a left foot strike, left foot launch, right foot launch, right foot strike, left foot z integral above a specified threshold, right foot z integral above a specified threshold, a left z integral below a threshold and a right foot z integral below a threshold. While a set of detected events may include all of specified events of the applicable template, a template match arises when the events satisfy the specified order and timing defined by the template constraints. As noted above, a match process may first identify that first and second predefined events exist. These events may correspond to jumping jack boundary events such as the left foot launch (start event) and a left foot strike (end event). The required timing for the other events may be specified as percentages of the duration between the detected left foot launch and the left foot strike. For example, the right launch event may be required to exist at 10% of the duration before the end event, i.e., the left foot strike event. The z integral events may correspond to a distance or a velocity depending on the type of sensor reading. In the example of an accelerometer, the z integral may correspond to foot velocity along the z-axis.

In some arrangements, various events may be designated within the template as optional, bonus or exclusion. Optional events may be detected for better event detection accuracy, for instance, while bonus events may correspond to better or more accurate performance of the corresponding action. Matching bonus events may improve a user's action performance quality score and/or provide rewards to the user (e.g., additional activity points or higher metrics). Exclusion events, as described, may specify when a series of events should be discounted or disregarded as a potential match with the jumping jack action template. For example, if a left foot strike event is detected between the left foot launch start event and the left foot strike end event, the series of events may be discarded as a potential match with a jumping jack action since the user's foot landed multiple times within the timespan.

A jumping jack activity type and/or template may further specify data sources from which sensor information is to be evaluated for event detection. Accordingly, an activity processing system may notify the sensor system of the types of data and data sources to monitor. In the above example of jumping jacks, the subscriptions may include foot strike and foot launch, x accelerations of one or more threshold values, two x integrals based on one or more threshold crossings and z acceleration derivatives having a max/min of a specified amount or threshold. Accordingly, the sensor system might only monitor sensors providing the above specified information and might only return events that correspond to the desired information and thresholds. For example, a foot strike having a contact pressure below a specified threshold might not be returned to the activity processing system as a foot strike event. The sensor system may also differentiate between foot strike events of a first threshold pressure and foot strike events of a second threshold pressure if multiple pressure thresholds are specified in the subscription. Various other configurations of sensor subscriptions may be defined as needed for particular types of activities.

FIG. 19 illustrates another example signal stream for right and left shoe-based sensors. The signal stream corresponds to an activity in which the user may perform a counter jump. Accordingly, the event labels noted in the graph may correspond to identification of portions of the signal stream that match a counter jump template, for instance.

FIG. 20 illustrates yet another example signal stream, where the user is performing a beep sprint drill/activity.

As described herein, in some arrangements, a sensor system used for activity monitoring and tracking may include force sensitive elements. Force sensitive elements may operate by detecting an amount of resistance within a circuit, which may vary based on an amount of pressure applied. Accordingly, a force sensitive sensor system may correlate a detected amount of resistance to a level of force or pressure by using a predefined look-up table. In some instances, however, the accuracy of a given table may decrease over time. Stated differently, the resistance-to-force profile of a sensor system may change over time. To compensate for such changes, the force sensitive sensor system may modify the force-to-pressure lookup table or select a new force-to-pressure lookup table.

To detect whether a force-to-pressure profile has changed within the force sensitive sensor system, the force sensitive sensor system may determine how much resistance is detected when a user's foot is on the ground and amount of resistance detected when the user's foot is off the ground. Based on this differential, a new force-to-pressure profile may be selected and used instead. In one example, the user may manually indicate when his or her foot is off and on the ground during a calibration mode. In other examples, the force sensitive sensor system may perform automatic self-calibration continuously and/or based on a predefined schedule or intervals. Various profiles may be defined based on empirical studies and analyses. In some arrangements, an average of a previous X number of steps or foot contact/foot non-contact event pairs may be analyzed to determine the resistance differential and to subsequently adjust the pressure profile. By modifying the pressure profile over time, the accuracy in detecting events and gauging various metrics may be enhanced.

Such calibration techniques are not limited to foot-based sensor systems. Other force sensitive sensor systems worn or used elsewhere on a user's body may also be calibrated using similar methods.

CONCLUSION

Providing an activity environment having one or more of the features described herein may provide a user with an experience that will encourage and motivate the user to engage in athletic activities and improve his or her fitness. Users may further communicate through social communities and challenge one another to participate in point challenges.

Aspects of the embodiments have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

We claim:

1. A computer-implemented method comprising:
    receiving, by a sensor system having at least a processor and a memory, raw sensor data associated with athletic activity of a user, the raw sensor data being received from one or more sensing devices;
    determining, by the sensor system and based on a signature of a signal received from the one or more sensing devices, a category of athletic activity being performed;
    selecting, by an activity processing system, a plurality of athletic activity templates for comparison, the plurality of athletic activity templates being selected based on the category of athletic activity being performed;
    comparing, by the activity processing system, one or more events in the raw sensor data to the selected plurality of activity templates;
    determining, by the activity processing system, whether the one or more events match one or more activity templates of the selected plurality of activity templates, wherein the determining includes evaluating whether a first candidate athletic activity meets one or more relative constraints of a first state, wherein the one or more relative constraints defines a required relationship between the first candidate athletic activity and a second candidate athletic activity;
    responsive to determining that the one or more events match one or more activity templates, classifying the one or more events of the user as performance of a first action of a first type; and
    determining, by the activity processing system, a quality of the first action, wherein determining the quality of the first action includes weighting at least one portion of the one or more matching activity templates more than at least one other portion of the one or more matching activity templates.

2. The computer-implemented method of claim 1, further including:
    determining, by the activity processing system, whether the quality of the first action is below a predetermined threshold; and
    responsive to determining that the quality of the first action is below the predetermined threshold, providing, by the activity processing system, coaching information to the user.

3. The computer-implemented method of claim 2, wherein the coaching information includes at least a coaching instruction related to heel weight.

4. The computer-implemented method of claim 2, wherein providing coaching information to the user further includes providing recommendations for improving the quality of the first type of action.

5. The computer-implemented method of claim 2, wherein the coaching information provided to the user is specific to at least one of the one or more events.

6. The computer-implemented method of claim 2, wherein the coaching information is generated based, at least in part, on data associated with weather and terrain at a location of performance of the athletic activity.

7. The computer-implemented method of claim 1, wherein determining the quality of the first action further includes determining a strength of a match between the one or more events and the one or more activity templates.

8. The computer-implemented method of claim 1, wherein at least one sensor of the one or more sensing devices is arranged in an article of footwear of the user.

9. One or more non-transitory computer readable media storing computer readable instructions that, when executed, cause at least one computing device to:
   determine a type of physical activity associated with an athletic activity performed by a user;
   based on the determined type of physical activity performed by the user, identify a plurality of activity templates associated with the physical activity;
   receive raw sensor data associated with the athletic activity performed by the user, the raw sensor data being received from one or more sensing devices;
   determine, based on a signature of a signal received from the one or more sensing devices, a category of athletic activity being performed;
   select a plurality of athletic activity templates for comparison, the plurality of athletic activity templates being selected based on the determined category of athletic activity being performed;
   compare one or more events in the raw sensor data to the selected plurality of activity templates;
   determine whether the one or more events match one or more activity templates of the selected plurality of activity templates, and evaluate whether a first candidate athletic activity meets one or more relative constraints of a first state, wherein the one or more relative constraints defines a required relationship between the first candidate athletic activity and a second candidate athletic activity;
   responsive to determining that the one or more events match one or more activity templates, classify the one or more events as performance of a first action of a first type; and
   determine a quality of the first action, wherein determining the quality of the first action further includes instructions that, when executed, cause the computing device to weight at least one portion of the one or more matching activity templates more than at least one other portion of the one or more matching activity templates.

10. The one or more non-transitory computer-readable media of claim 9, further including instructions that, when executed, cause the computing device to:
    determine whether the quality of the first action is below a predetermined threshold; and
    responsive to determining that the quality of the first action is below the predetermined threshold, provide coaching information to the user.

11. The one or more non-transitory computer-readable media of claim 10, wherein providing coaching information to the user further includes instructions that, when executed, cause the computing device to:
    provide recommendations for improving the quality of the first type of action.

12. The one or more non-transitory computer-readable media of claim 10, wherein the coaching information provided to the user is specific to at least one of the one or more events.

13. The one or more non-transitory computer-readable media of claim 9, further including instructions that, when executed, cause the computer device to:
    responsive to determining that the one or more events do not match one or more activity templates, storing the received sensor data.

14. The one or more non-transitory computer-readable media of claim 9, wherein determining the quality of the first action further includes instructions that, when executed, cause the computing device to:
    determine a strength of a match between the one or more events and the one or more activity templates.

15. The one or more non-transitory computer-readable media of claim 9, wherein at least one sensor of the one or more sensing devices is arranged in an article of footwear of the user.

16. A system comprising:
    a sensor system including a plurality of sensors, the sensor system further including:
       a first processor; and
       memory storing computer readable instructions that, when executed, cause the first processor to:
          receive raw sensor data associated with athletic activity of a user;
          determine, based on a signature of a signal received from the plurality of sensors, a category of athletic activity being performed; and
          transmit, to an activity processing system, the determined category of athletic activity being performed and the raw sensor data; and
    the activity processing system, including:
       a second processor; and
       memory storing computer-readable instructions that, when executed, cause the second processor to:
          receive the transmitted determined category of athletic activity being performed;
          select a plurality of athletic activity templates for comparison, the plurality of athletic activity templates being selected based on the determined category of athletic activity being performed;
          compare one or more events detected in the raw sensor data to the selected plurality of activity templates;
          determine whether the one or more events match one or more activity templates of the selected plurality of activity templates, and evaluating whether a first candidate athletic activity meets one or more relative constraints of a first state, wherein the one or more relative constraints defines a required relationship between the first candidate athletic activity and a second candidate athletic activity;
          responsive to determining that the one or more events match one or more activity templates, classify the one or more events of the user as performance of a first action of a first type; and
          determine a quality of the first action, wherein determining the quality of the first action includes instructions that, when executed, cause the second processor to weight at least one portion of the one or more matching activity templates more than at least one other portion of the one or more matching activity templates.

17. The system of claim 16, further including instructions that, when executed, cause the second processor to:
   determine whether the quality of the first action is below a predetermined threshold; and
   responsive to determining that the quality of the first action is below the predetermined threshold, provide coaching information to the user.

18. The system of claim 17, wherein determining the quality of the first action further includes instructions that, when executed, cause the second processor to:
   determine a strength of a match between the one or more events and the one or more activity templates.

19. The system of claim 16, wherein at least one sensor of the sensor system is arranged in an article of footwear of the user.

20. The system of claim 17, wherein the coaching information provided to the user is specific to at least one of the one or more events.

\* \* \* \* \*